(12) United States Patent
Matsuo

(10) Patent No.: US 8,440,853 B2
(45) Date of Patent: May 14, 2013

(54) ESTER COMPOUND AND USE THEREOF

(75) Inventor: Noritada Matsuo, Amagasaki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/580,439

(22) PCT Filed: Feb. 18, 2011

(86) PCT No.: PCT/JP2011/054221
§ 371 (c)(1),
(2), (4) Date: Aug. 22, 2012

(87) PCT Pub. No.: WO2011/105524
PCT Pub. Date: Sep. 1, 2011

(65) Prior Publication Data
US 2012/0322870 A1    Dec. 20, 2012

(30) Foreign Application Priority Data

Feb. 25, 2010   (JP) ................. 2010-039982

(51) Int. Cl.
*C07C 255/00* (2006.01)
*A01N 37/34* (2006.01)

(52) U.S. Cl.
USPC .......................................... 558/407; 514/521

(58) Field of Classification Search .... 558/407; 514/521
See application file for complete search history.

(56) References Cited

U.S. PATENT DOCUMENTS 4,602,038 A    7/1986   Tessier et al.
5,135,951 A    8/1992   Babin et al.

FOREIGN PATENT DOCUMENTS

| JP | 58-85856 A | 5/1983 |
| JP | 60-016962 A | 1/1985 |
| WO | 2008/111627 A1 | 9/2008 |

*Primary Examiner* — Jafar Parsa
(74) *Attorney, Agent, or Firm* — Sughrue Mion, PLLC

(57) ABSTRACT

An ester compound represented by formula (1):
wherein $R^2$ represents hydrogen, fluorine, C1-C4 alkyl, C1-C4 alkoxy, C1-C4 alkoxymethyl, or C1-C4 alkylthiomethyl; and $R^2$ represents $C_1$-$C_4$ alkyl, has an excellent pest control effect and is therefore useful as an active ingredient of a pest control agent.

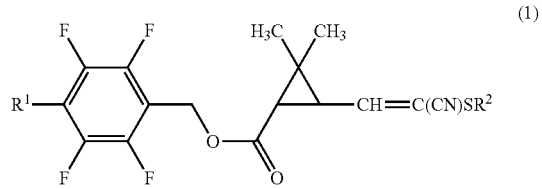

(1)

22 Claims, No Drawings

ESTER COMPOUND AND USE THEREOF

CROSS REFERENCE TO RELATED APPLICATIONS

This application is a National Stage of International Application No. PCT/JP2011/054221 filed Feb. 18, 2011, claiming priority based on Japanese Patent Application No. 2010-039982 filed Feb. 25, 2010, the contents of all of which are incorporated herein by reference in their entirety.

TECHNICAL FIELD

The present invention relates to an ester compound and use thereof.

BACKGROUND ART

Heretofore, various compounds have been synthesized so as to control pests. For example, a certain ester compound is described in JP-A-60-16962.

DISCLOSURE OF INVENTION

An object of the present invention is to provide a novel compound having an excellent pest control effect.

The present inventors have intensively studied and found that an ester compound represented by formula (1) shown below has an excellent pest control effect, and led to the present invention.

That is, the present invention is directed to the following invention:

[1] An ester compound represented by formula (1):

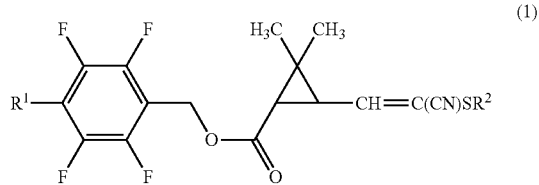

wherein $R^2$ represents hydrogen, fluorine, C1-C4 alkyl, C1-C4 alkoxy, C1-C4 alkoxymethyl, or C1-C4 alkylthiomethyl; and $R^2$ represents $C_1$-$C_4$ alkyl,
(hereinafter referred to as the compound of the present invention);
[2] The ester compound according to [1], wherein a relative configuration of the substituent at the 1-position of the cyclopropane ring and the substituent at the 3-position of the cyclopropane ring is a trans configuration in formula (1);
[3] The ester compound according to [1], wherein an absolute configuration of the 1-position of the cyclopropane ring is an R configuration in formula (1);
[4] The ester compound according to [1], wherein an absolute configuration of the 1-position of the cyclopropane ring is an R configuration, and a relative configuration of the substituent at the 1-position of the cyclopropane ring and the substituent at the 3-position of the cyclopropane ring is a trans configuration in formula (1);
[5] The ester compound according to any one of [1] to [4], wherein a double bond of the substituent at the 3-position of the cyclopropane ring is in the E configuration or a mixture of E configuration and Z configuration, and the proportion of the E configuration is 50% or more in formula (1);
[6] The ester compound according to any one of [1] to [4], a double bond of the substituent at the 3-position of the cyclopropane ring is in the E configuration in formula (1);
[7] The ester compound according to any one of [1] to [4], wherein $R^2$ is methyl in formula (1);
[8] The ester compound according to any one of [1] to [4], wherein $R^2$ is ethyl in formula (1);
[9] The ester compound according to [5], wherein $R^2$ is methyl in formula (1);
[10] The ester compound according to [5], wherein $R^2$ is ethyl in formula (1);
[11] The ester compound according to [6], wherein $R^2$ is methyl in formula (1);
[12] The ester compound according to [6], wherein $R^2$ is ethyl in formula (1);
[13] The ester compound according to any one of [1] to [4], wherein $R^2$ is methoxymethyl in formula (1);
[14] The ester compound according to any one of [1] to [4], wherein $R^2$ is methyl in formula (1);
[15] The ester compound according to any one of [1] to [4], wherein $R^2$ is methoxy in formula (1);
[16] The ester compound according to any one of [1] to [4], wherein $R^2$ is hydrogen in formula (1);
[17] A pest control agent comprising the ester compound according to any one of [1] to [16] and an inert carrier;
[18] A method of controlling pests, which comprises a step of applying an effective amount of the ester compound according to any one of [1] to [16] to pests or a place where pests habitat;
[19] A method of controlling pests, which comprises the step of applying an effective amount of the ester compound according to any one of [1] to [16] to cockroaches or a place where cockroaches inhabits;
[20] The method of controlling pests according to [19], wherein the cockroach is American cockroach (*Periplaneta Americana*);
[21] The method of controlling pests according to [19], wherein the cockroach is German cockroach (*Blattella germanica*);
[22] A method of controlling pests, which comprises a step of spraying an effective amount of the ester compound according to any one of [1] to [16] to cockroaches or a place where cockroaches inhabit;
[23] The method of controlling pests according to [22], wherein the cockroach is American cockroach (*Periplaneta Americana*);
[24] The method of controlling pests according to [22], wherein the cockroach is German cockroach (*Blattella germanica*).

[1-a] An ester compound represented by formula (1-a):

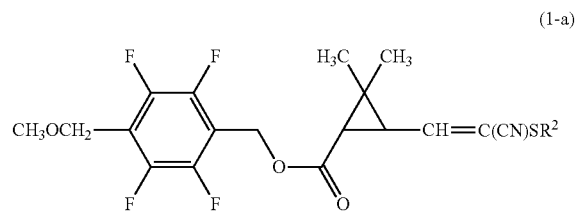

wherein $R^2$ represents $C_1$-$C_4$ alkyl;
[2-a] The ester compound according to [1-a], wherein a relative configuration of the substituent at the 1-position of the cyclopropane ring and the substituent at the 3-position of the cyclopropane ring is a trans configuration in formula (1-a);
[3-a] The ester compound according to [1-a], wherein an absolute configuration of the 1-position of the cyclopropane ring is an R configuration in formula (1-a);

[4-a] The ester compound according to [1-a], wherein an absolute configuration of the 1-position of the cyclopropane ring is an R configuration, and a relative configuration of the substituent at the 1-position of the cyclopropane ring and the substituent at the 3-position of the cyclopropane ring is a trans configuration in formula (1-a);

[5-a] The ester compound according to any one of [1-a] to [4-a], wherein a double bond of the substituent at the 3-position of the cyclopropane ring is in the E configuration or a mixture of E configuration and Z configuration, and the proportion of the E configuration is 50% or more in formula (1-a);

[6-a] The ester compound according to any one of [1-a] to [4-a], a double bond of the substituent at the 3-position of the cyclopropane ring is in the E configuration in formula (1-a);

[7-a] The ester compound according to any one of [1-a] to [4-a], wherein $R^2$ is methyl in formula (1-a);

[8-a] The ester compound according to any one of [1-a] to [4-a], wherein $R^2$ is ethyl in formula (1-a);

[9-a] The ester compound according to [5-a], wherein $R^2$ is methyl in formula (1-a);

[10-a] The ester compound according to [5-a], wherein $R^2$ is ethyl in formula (1-a);

[11-a] The ester compound according to [6-a], wherein $R^2$ is methyl in formula (1-a);

[12-a] The ester compound according to [6-a], wherein $R^2$ is ethyl in formula (1-a);

[13-a] A pest control agent comprising the ester compound according to any one of [1-a] to [12-a] and an inert carrier;

[14-a] A method of controlling pests, which comprises a step of applying an effective amount of the ester compound according to any one of [1-a] to [12-a] to pests or a place where pests habitat;

[15-a] A method of controlling pests, which comprises the step of applying an effective amount of the ester compound according to any one of [1-a] to [12-a] to cockroaches or a place where cockroaches inhabits;

[16-a] The method of controlling pests according to [15-a], wherein the cockroach is American cockroach (*Periplaneta Americana*);

[17-a] The method of controlling pests according to [15-a], wherein the cockroach is German cockroach (*Blattella germanica*);

[18-a] A method of controlling pests, which comprises a step of spraying an effective amount of the ester compound according to any one of [1-a] to [12-a] to cockroaches or a place where cockroaches inhabit;

[19-a] The method of controlling pests according to [18-a], wherein the cockroach is American cockroach (*Periplaneta Americana*);

[20-a] The method of controlling pests according to [18-a], wherein the cockroach is German cockroach (*Blattella germanica*);

[1-b] An ester compound represented by formula (1-b):

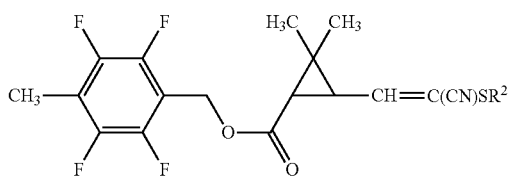

(1-b)

wherein $R^2$ represents $C_1$-$C_4$ alkyl;

[2-b] The ester compound according to [1-b], wherein a relative configuration of the substituent at the 1-position of the cyclopropane ring and the substituent at the 3-position of the cyclopropane ring is a trans configuration in formula (1-b);

[3-b] The ester compound according to [1-b], wherein an absolute configuration of the 1-position of the cyclopropane ring is an R configuration in formula (1-b);

[4-b] The ester compound according to [1-b], wherein an absolute configuration of the 1-position of the cyclopropane ring is an R configuration, and a relative configuration of the substituent at the 1-position of the cyclopropane ring and the substituent at the 3-position of the cyclopropane ring is a trans configuration in formula (1-b);

[5-b] The ester compound according to any one of [1-b] to [4-b], wherein a double bond of the substituent at the 3-position of the cyclopropane ring is in the E configuration or a mixture of E configuration and Z configuration, and the proportion of the E configuration is 50% or more in formula (1-b);

[6-b] The ester compound according to any one of [1-b] to [4-b], a double bond of the substituent at the 3-position of the cyclopropane ring is in the E configuration in formula (1-b);

[7-b] The ester compound according to any one of [1-b] to [4-b], wherein $R^2$ is methyl in formula (1-b);

[8-b] The ester compound according to any one of [1-b] to [4-b], wherein $R^2$ is ethyl in formula (1-b);

[9-b] The ester compound according to [5-b], wherein $R^2$ is methyl in formula (1-b);

[10-b] The ester compound according to [5-b], wherein $R^2$ is ethyl in formula (1-b);

[11-b] The ester compound according to [6-b], wherein $R^2$ is methyl in formula (1-b);

[12-b] The ester compound according to [6-b], wherein $R^2$ is ethyl in formula (1-b);

[13-b] A pest control agent comprising the ester compound according to any one of [1-b] to [12-b] and an inert carrier;

[14-b] A method of controlling pests, which comprises a step of applying an effective amount of the ester compound according to any one of [1-b] to [12-b] to pests or a place where pests habitat;

[15-b] A method of controlling pests, which comprises the step of applying an effective amount of the ester compound according to any one of [1-b] to [12-b] to cockroaches or a place where cockroaches inhabits;

[16-b] The method of controlling pests according to [15-b], wherein the cockroach is American cockroach (*Periplaneta Americana*);

[17-b] The method of controlling pests according to [15-b], wherein the cockroach is German cockroach (*Blattella germanica*);

[18-b] A method of controlling pests, which comprises a step of spraying an effective amount of the ester compound according to any one of [1-b] to [12-b] to cockroaches or a place where cockroaches inhabit;

[19-b] The method of controlling pests according to [18-b], wherein the cockroach is American cockroach (*Periplaneta Americana*);

[20-b] The method of controlling pests according to [18-b], wherein the cockroach is German cockroach (*Blattella germanica*);

[1-c] An ester compound represented by formula (1-c):

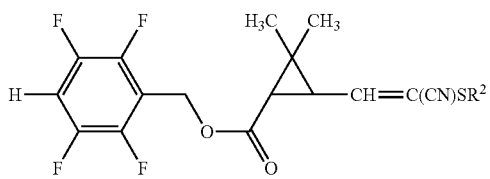

wherein $R^2$ represents $C_1$-$C_4$ alkyl;
[2-c] The ester compound according to [1-c], wherein a relative configuration of the substituent at the 1-position of the cyclopropane ring and the substituent at the 3-position of the cyclopropane ring is a trans configuration in formula (1-c);
[3-c] The ester compound according to [1-c], wherein an absolute configuration of the 1-position of the cyclopropane ring is an R configuration in formula (1-c);
[4-c] The ester compound according to [1-c], wherein an absolute configuration of the 1-position of the cyclopropane ring is an R configuration, and a relative configuration of the substituent at the 1-position of the cyclopropane ring and the substituent at the 3-position of the cyclopropane ring is a trans configuration in formula (1-c);
[5-c] The ester compound according to any one of [1-c] to [4-c], wherein a double bond of the substituent at the 3-position of the cyclopropane ring is in the E configuration or a mixture of E configuration and Z configuration, and the proportion of the E configuration is 50% or more in formula (1-c);
[6-c] The ester compound according to any one of [1-c] to [4-c], a double bond of the substituent at the 3-position of the cyclopropane ring is in the E configuration in formula (1-c);
[7-c] The ester compound according to any one of [1-c] to [4-c], wherein $R^2$ is methyl in formula (1-c);
[8-c] The ester compound according to any one of [1-c] to [4-c], wherein $R^2$ is ethyl in formula (1-c);
[9-c] The ester compound according to [5-c], wherein $R^2$ is methyl in formula (1-c);
[10-c] The ester compound according to [5-c], wherein $R^2$ is ethyl in formula (1-c);
[11-c] The ester compound according to [6-c], wherein $R^2$ is methyl in formula (1-c);
[12-c] The ester compound according to [6-c], wherein $R^2$ is ethyl in formula (1-c);
[13-c] A pest control agent comprising the ester compound according to any one of [1-c] to [12-c] and an inert carrier;
[14-c] A method of controlling pests, which comprises a step of applying an effective amount of the ester compound according to any one of [1-c] to [12-c] to pests or a place where pests habitat;
[15-c] A method of controlling pests, which comprises the step of applying an effective amount of the ester compound according to any one of [1-c] to [12-c] to cockroaches or a place where cockroaches inhabits;
[16-c] The method of controlling pests according to [15-c], wherein the cockroach is American cockroach (*Periplaneta Americana*);
[17-c] The method of controlling pests according to [15-c], wherein the cockroach is German cockroach (*Blattella germanica*);
[18-c] A method of controlling pests, which comprises a step of spraying an effective amount of the ester compound according to any one of [1-c] to [12-c] to cockroaches or a place where cockroaches inhabit;
[19-c] The method of controlling pests according to [18-c], wherein the cockroach is American cockroach (*Periplaneta Americana*); and
[20-c] The method of controlling pests according to [18-c], wherein the cockroach is German cockroach (*Blattella germanica*).

The compound of the present invention has an excellent pest control effect and is therefore useful as an active ingredient of a pest control agent.

In the compound of the present invention, there are isomers derived from two asymmetric carbon atoms at the 1-position and the 3-position on the cyclopropane ring, and isomers derived from the double bond present in the substituent at the 3-position of the cyclopropane ring. Each isomer having pest control activity or a mixture of those isomers in an arbitrary ratio which has pest control activity are included in the present invention.

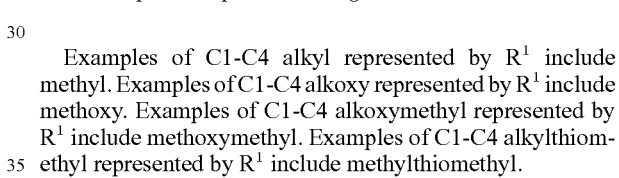

Examples of C1-C4 alkyl represented by $R^1$ include methyl. Examples of C1-C4 alkoxy represented by $R^1$ include methoxy. Examples of C1-C4 alkoxymethyl represented by $R^1$ include methoxymethyl. Examples of C1-C4 alkylthiomethyl represented by $R^1$ include methylthiomethyl.

Examples of the $C_1$-$C_4$ alkyl represented by $R^2$ include methyl, ethyl, propyl, butyl and isopropyl.

Examples of the compound of the present invention include the following compounds.
A compound represented by formula (1) in which a relative configuration of the substituent at the 1-position of the cyclopropane ring and the substituent at the 3-position of the cyclopropane ring is a trans configuration;
A compound represented by formula (1) in which the absolute configuration of the 1-position of the cyclopropane ring is an R configuration;
A compound represented by formula (1) in which an absolute configuration of the 1-position of the cyclopropane ring is an R configuration, and a relative configuration of the substituent at the 1-position of the cyclopropane ring and the substituent at the 3-position of the cyclopropane ring is a trans configuration;
A compound represented by formula (1) in which the double bond of the substituent at the 3-position of the cyclopropane ring is in the E configuration or a mixture of E configuration and Z configuration, and the proportion of the E configuration is 50% or more;
A compound represented by formula (1) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, and the proportion of the E configuration is 50% or more;
A compound represented by formula (1) in which absolute configuration of the 1-position of the cyclopropane ring is an R configuration, the double bond of the substituent at the 3-position of the cyclopropane ring is in the E configuration or a mixture of E configuration and Z configuration, and the proportion of the E configuration is 50% or more;

A compound represented by formula (1) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, and the proportion of the E configuration is 50% or more;

A compound represented by formula (1) in which the double bond of the substituent at the 3-position of the cyclopropane ring is in the E configuration.

A compound represented by formula (1) in which a relative configuration of the substituent at the 1-position of the cyclopropane ring and the substituent at the 3-position of the cyclopropane ring is a trans configuration, and the double bond of the substituent at the 3-position of the cyclopropane ring is in the E configuration.

A compound represented by formula (1) in which absolute configuration of the 1-position of the cyclopropane ring is an R configuration, and the double bond of the substituent at the 3-position of the cyclopropane ring is in the E configuration.

A compound represented by formula (1) in which absolute configuration of the 1-position of the cyclopropane ring is an R configuration, a relative configuration of the substituent at the 1-position of the cyclopropane ring and the substituent at the 3-position of the cyclopropane ring is a trans configuration, and the double bond of the substituent at the 3-position of the cyclopropane ring is in the E configuration.

A compound represented by formula (1) in which a relative configuration of the substituent at the 1-position of the cyclopropane ring and the substituent at the 3-position of the cyclopropane ring is a trans configuration, and $R^2$ is methyl;

A compound represented by formula (1) in which absolute configuration of the 1-position of the cyclopropane ring is an R configuration, and $R^2$ is methyl;

A compound represented by formula (1) in which absolute configuration of the 1-position of the cyclopropane ring is an R configuration, a relative configuration of the substituent at the 1-position of the cyclopropane ring and the substituent at the 3-position of the cyclopropane ring is a trans configuration, and $R^2$ is methyl;

A compound represented by formula (1) in which the double bond of the substituent at the 3-position of the cyclopropane ring is in the E configuration or a mixture of E configuration and Z configuration, the proportion of the E configuration is 50% or more, and $R^2$ is methyl;

A compound represented by formula (1) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more, and $R^2$ is methyl;

A compound represented by formula (1) in which absolute configuration of the 1-position of the cyclopropane ring is an R configuration, the double bond of the substituent at the 3-position of the cyclopropane ring is in the E configuration or a mixture of E configuration and Z configuration, the proportion of the E configuration is 50% or more, and $R^2$ is methyl;

A compound represented by formula (1) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more, and $R^2$ is methyl;

A compound represented by formula (1) in which the double bond of the substituent at the 3-position of the cyclopropane ring is in the E configuration, and $R^2$ is methyl.

A compound represented by formula (1) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration, and $R^2$ is methyl.

A compound represented by formula (1) in which absolute configuration of the 1-position of the cyclopropane ring is an R configuration, the double bond of the substituent at the 3-position of the cyclopropane ring is in the E configuration, and $R^2$ is methyl.

A compound represented by formula (1) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration, and $R^2$ is methyl.

A compound represented by formula (1) in which a relative configuration of the substituent at the 1-position of the cyclopropane ring and the substituent at the 3-position of the cyclopropane ring is a trans configuration, and $R^2$ is ethyl;

A compound represented by formula (1) in which absolute configuration of the 1-position of the cyclopropane ring is an R configuration, and $R^2$ is ethyl;

A compound represented by formula (1) in which absolute configuration of the 1-position of the cyclopropane ring is an R configuration, a relative configuration of the substituent at the 1-position of the cyclopropane ring and the substituent at the 3-position of the cyclopropane ring is a trans configuration, and $R^2$ is ethyl;

A compound represented by formula (1) in which the double bond of the substituent at the 3-position of the cyclopropane ring is in the E configuration or a mixture of E configuration and Z configuration, the proportion of the E configuration is 50% or more, and $R^2$ is ethyl;

A compound represented by formula (1) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more, and $R^2$ is ethyl;

A compound represented by formula (1) in which absolute configuration of the 1-position of the cyclopropane ring is an R configuration, the double bond of the substituent at the 3-position of the cyclopropane ring is in the E configuration or a mixture of E configuration and Z configuration, the proportion of the E configuration is 50% or more, and $R^2$ is ethyl;

A compound represented by formula (1) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more, and $R^2$ is ethyl;

A compound represented by formula (1) in which the double bond of the substituent at the 3-position of the cyclopropane ring is in the E configuration, and $R^2$ is ethyl.

A compound represented by formula (1) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration, and $R^2$ is ethyl.

A compound represented by formula (1) in which absolute configuration of the 1-position of the cyclopropane ring is an R configuration, the double bond of the substituent at the 3-position of the cyclopropane ring is in the E configuration, and $R^2$ is ethyl.

A compound represented by formula (1) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration, and $R^2$ is ethyl.

A compound represented by formula (1) in which a relative configuration of the substituent at the 1-position of the cyclopropane ring and the substituent at the 3-position of the cyclopropane ring is a cis configuration;

A compound represented by formula (1) in which absolute configuration of the 1-position of the cyclopropane ring is an R configuration, and a relative configuration of the substituent at the 1-position of the cyclopropane ring and the substituent at the 3-position of the cyclopropane ring is a cis configuration;

A compound represented by formula (1) in which a relative configuration of the substituent at the 1-position of the cyclopropane ring and the substituent at the 3-position of the cyclopropane ring is a cis configuration, and the double bond of the substituent at the 3-position of the cyclopropane ring is in the E configuration; and A compound represented by formula (1) in which absolute configuration of the 1-position of the cyclopropane ring is an R configuration, a relative configuration of the substituent at the 1-position of the cyclopropane ring and the substituent at the 3-position of the cyclopropane ring is a cis configuration, and the double bond of the substituent at the 3-position of the cyclopropane ring is in the E configuration.

A compound represented by formula (1-a) in which a relative configuration of the substituent at the 1-position of the cyclopropane ring and the substituent at the 3-position of the cyclopropane ring is a trans configuration;

A compound represented by formula (1-a) in which the absolute configuration of the 1-position of the cyclopropane ring is an R configuration;

A compound represented by formula (1-a) in which an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by formula (1-a) in which the double bond of the substituent at the 3-position of the cyclopropane ring is in the E configuration or a mixture of E configuration and Z configuration, and the proportion of the E configuration is 50% or more;

A compound represented by formula (1-a) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, and the proportion of the E configuration is 50% or more;

A compound represented by formula (1-a) in which absolute configuration of the 1-position of the cyclopropane ring is an R configuration, the double bond of the substituent at the 3-position of the cyclopropane ring is in the E configuration or a mixture of E configuration and Z configuration, and the proportion of the E configuration is 50% or more;

A compound represented by formula (1-a) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, and the proportion of the E configuration is 50% or more;

A compound represented by formula (1-a) in which the double bond of the substituent at the 3-position of the cyclopropane ring is in the E configuration.

A compound represented by formula (1-a) in which a relative configuration of the substituent at the 1-position of the cyclopropane ring and the substituent at the 3-position of the cyclopropane ring is a trans configuration, and the double bond of the substituent at the 3-position of the cyclopropane ring is in the E configuration.

A compound represented by formula (1-a) in which absolute configuration of the 1-position of the cyclopropane ring is an R configuration, and the double bond of the substituent at the 3-position of the cyclopropane ring is in the E configuration.

A compound represented by formula (1-a) in which absolute configuration of the 1-position of the cyclopropane ring is an R configuration, a relative configuration of the substituent at the 1-position of the cyclopropane ring and the substituent at the 3-position of the cyclopropane ring is a trans configuration, and the double bond of the substituent at the 3-position of the cyclopropane ring is in the E configuration.

A compound represented by formula (1-a) in which a relative configuration of the substituent at the 1-position of the cyclopropane ring and the substituent at the 3-position of the cyclopropane ring is a trans configuration, and $R^2$ is methyl;

A compound represented by formula (1-a) in which absolute configuration of the 1-position of the cyclopropane ring is an R configuration, and $R^2$ is methyl;

A compound represented by formula (1-a) in which absolute configuration of the 1-position of the cyclopropane ring is an R configuration, a relative configuration of the substituent at the 1-position of the cyclopropane ring and the substituent at the 3-position of the cyclopropane ring is a trans configuration, and $R^2$ is methyl;

A compound represented by formula (1-a) in which the double bond of the substituent at the 3-position of the cyclopropane ring is in the E configuration or a mixture of E configuration and Z configuration, the proportion of the E configuration is 50% or more, and $R^2$ is methyl;

A compound represented by formula (1-a) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more, and $R^2$ is methyl;

A compound represented by formula (1-a) in which absolute configuration of the 1-position of the cyclopropane ring is an R configuration, the double bond of the substituent at the 3-position of the cyclopropane ring is in the E configuration or a mixture of E configuration and Z configuration, the proportion of the E configuration is 50% or more, and $R^2$ is methyl;

A compound represented by formula (1-a) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more, and $R^2$ is methyl;

A compound represented by formula (1-a) in which the double bond of the substituent at the 3-position of the cyclopropane ring is in the E configuration, and $R^2$ is methyl.

A compound represented by formula (1-a) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration, and $R^2$ is methyl.

A compound represented by formula (1-a) in which absolute configuration of the 1-position of the cyclopropane ring is an R configuration, the double bond of the substituent at the 3-position of the cyclopropane ring is in the E configuration, and $R^2$ is methyl.

A compound represented by formula (1-a) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration, and $R^2$ is methyl.

A compound represented by formula (1-a) in which a relative configuration of the substituent at the 1-position of the cyclopropane ring and the substituent at the 3-position of the cyclopropane ring is a trans configuration, and $R^2$ is ethyl;

A compound represented by formula (1-a) in which absolute configuration of the 1-position of the cyclopropane ring is an R configuration, and $R^2$ is ethyl;

A compound represented by formula (1-a) in which absolute configuration of the 1-position of the cyclopropane ring is an R configuration, a relative configuration of the substituent at the 1-position of the cyclopropane ring and the substituent at the 3-position of the cyclopropane ring is a trans configuration, and $R^2$ is ethyl;

A compound represented by formula (1-a) in which the double bond of the substituent at the 3-position of the cyclopropane ring is in the E configuration or a mixture of E configuration and Z configuration, the proportion of the E configuration is 50% or more, and $R^2$ is ethyl;

A compound represented by formula (1-a) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more, and $R^2$ is ethyl;

A compound represented by formula (1-a) in which absolute configuration of the 1-position of the cyclopropane ring is an R configuration, the double bond of the substituent at the 3-position of the cyclopropane ring is in the E configuration or a mixture of E configuration and Z configuration, the proportion of the E configuration is 50% or more, and $R^2$ is ethyl;

A compound represented by formula (1-a) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more, and $R^2$ is ethyl;

A compound represented by formula (1-a) in which the double bond of the substituent at the 3-position of the cyclopropane ring is in the E configuration, and $R^2$ is ethyl.

A compound represented by formula (1-a) in which a relative configuration of the substituent at the 1-position of the cyclopropane ring and the substituent at the 3-position of the cyclopropane ring is a trans configuration, the double bond of the substituent at the 3-position of the cyclopropane ring is in the E configuration, and $R^2$ is ethyl.

A compound represented by formula (1-a) in which absolute configuration of the 1-position of the cyclopropane ring is an R configuration, the double bond of the substituent at the 3-position of the cyclopropane ring is in the E configuration, and $R^2$ is ethyl.

A compound represented by formula (1-a) in which absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration, and $R^2$ is ethyl.

A compound represented by formula (1-a) in which a relative configuration of the substituent at the 1-position of the cyclopropane ring and the substituent at the 3-position of the cyclopropane ring is a cis configuration;

A compound represented by formula (1-a) in which absolute configuration of the 1-position of the cyclopropane ring is an R configuration, and a relative configuration of the substituent at the 1-position of the cyclopropane ring and the substituent at the 3-position of the cyclopropane ring is a cis configuration;

A compound represented by formula (1-a) in which a relative configuration of the substituent at the 1-position of the cyclopropane ring and the substituent at the 3-position of the cyclopropane ring is a cis configuration, and the double bond of the substituent at the 3-position of the cyclopropane ring is in the E configuration;

A compound represented by formula (1-a) in which absolute configuration of the 1-position of the cyclopropane ring is an R configuration, a relative configuration of the substituent at the 1-position of the cyclopropane ring and the substituent at the 3-position of the cyclopropane ring is a cis configuration, and the double bond of the substituent at the 3-position of the cyclopropane ring is in the E configuration;

A compound represented by formula (1-b) in which $R^2$ is methyl and a relative configuration of the substituent at the 1-position of the cyclopropane ring and the substituent at the 3-position of the cyclopropane ring is a trans configuration;

A compound represented by formula (1-b) in which $R^2$ is methyl and absolute configuration of the 1-position of the cyclopropane ring is an R configuration;

A compound represented by formula (1-b) in which $R^2$ is methyl and absolute configuration of the 1-position of the cyclopropane ring is an R configuration, a relative configuration of the substituent at the 1-position of the cyclopropane ring and the substituent at the 3-position of the cyclopropane ring is a trans configuration;

A compound represented by formula (1-b) in which $R^2$ is methyl and the double bond of the substituent at the 3-position of the cyclopropane ring is in the E configuration or a mixture of E configuration and Z configuration, the proportion of the E configuration is 50% or more;

A compound represented by formula (1-b) in which $R^2$ is methyl and a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more;

A compound represented by formula (1-b) in which $R^2$ is methyl and absolute configuration of the 1-position of the cyclopropane ring is an R configuration, the double bond of the substituent at the 3-position of the cyclopropane ring is in the E configuration or a mixture of E configuration and Z configuration, the proportion of the E configuration is 50% or more;

A compound represented by formula (1-b) in which $R^2$ is methyl and absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more;

A compound represented by formula (1-b) in which $R^2$ is methyl and the double bond of the substituent at the 3-position of the cyclopropane ring is in the E configuration;

A compound represented by formula (1-c) in which $R^2$ is methyl and a relative configuration of the substituent at the 1-position of the cyclopropane ring and the substituent at the 3-position of the cyclopropane ring is a trans configuration, the double bond of the substituent at the 3-position of the cyclopropane ring is in the E configuration.

A compound represented by formula (1-c) in which $R^2$ is methyl and absolute configuration of the 1-position of the cyclopropane ring is an R configuration, the double bond of the substituent at the 3-position of the cyclopropane ring is in the E configuration.

A compound represented by formula (1-c) in which $R^2$ is ethyl and a relative configuration of the substituent at the 1-position of the cyclopropane ring and the substituent at the 3-position of the cyclopropane ring is a trans configuration;

A compound represented by formula (1-c) in which $R^2$ is ethyl and absolute configuration of the 1-position of the cyclopropane ring is an R configuration;

A compound represented by formula (1-c) in which $R^2$ is ethyl and absolute configuration of the 1-position of the cyclopropane ring is an R configuration, a relative configuration of the substituent at the 1-position of the cyclopropane ring and the substituent at the 3-position of the cyclopropane ring is a trans configuration;

A compound represented by formula (1-c) in which $R^2$ is ethyl and the double bond of the substituent at the 3-position of the cyclopropane ring is in the E configuration or a mixture of E configuration and Z configuration, the proportion of the E configuration is 50% or more;

A compound represented by formula (1-c) in which $R^2$ is ethyl and a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more;

A compound represented by formula (1-c) in which $R^2$ is ethyl and absolute configuration of the 1-position of the cyclopropane ring is an R configuration, the double bond of the substituent at the 3-position of the cyclopropane ring is in the E configuration or a mixture of E configuration and Z configuration, the proportion of the E configuration is 50% or more;

A compound represented by formula (1-c) in which $R^2$ is ethyl and absolute configuration of the 1-position of the cyclopropane ring is an R configuration, a relative configuration of the substituent at the 1-position of the cyclopropane ring and the substituent at the 3-position of the cyclopropane ring is a trans configuration, the double bond of the substituent at the 3-position of the cyclopropane ring is in the E configuration or a mixture of E configuration and Z configuration, the proportion of the E configuration is 50% or more;

A compound represented by formula (1-c) in which $R^2$ is ethyl and the double bond of the substituent at the 3-position of the cyclopropane ring is in the E configuration.

A compound represented by formula (1-c) in which $R^2$ is ethyl and a relative configuration of the substituent at the 1-position of the cyclopropane ring and the substituent at the 3-position of the cyclopropane ring is a trans configuration, the double bond of the substituent at the 3-position of the cyclopropane ring is in the E configuration.

A compound represented by formula (1-c) in which $R^2$ is ethyl and absolute configuration of the 1-position of the cyclopropane ring is an R configuration, the double bond of the substituent at the 3-position of the cyclopropane ring is in the E configuration.

The method for producing the compound of the present invention will be described below.

The compound of the present invention can be produced, for example, by the following process.

(Production Process 1)

A process of reacting an alcohol compound represented by formula (2):

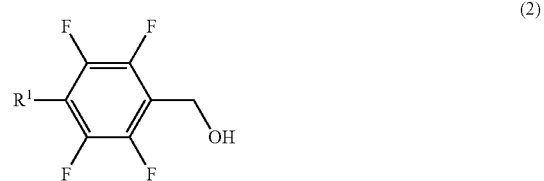

(2)

wherein $R^1$ represents the same meanings as described above, with a carboxylic acid compound represented by formula (3):

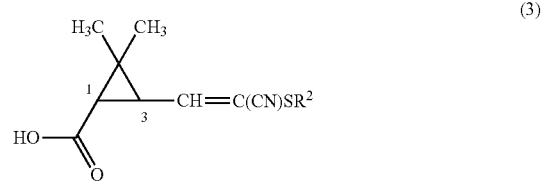

(3)

wherein $R^2$ represents the same meanings as described above, or a reactive derivative thereof.

Examples of the reactive derivative include an acid halide of the carboxylic acid compound represented by formula (3), an acid anhydride of the carboxylic acid compound represented by formula (3), an ester of the carboxylic acid compound represented by formula (3) and so on. Examples of the acid halide include an acid chloride compound and an acid bromide compound, and examples of the ester include a methyl ester, an ethyl ester and so on.

The reaction is usually conducted in a solvent in the presence of a condensing agent or a base.

Examples of the condensing agent used in the reaction include dicyclohexylcarbodiimide and 1-ethyl-3-(3-dimethylaminopropyl)carbodiimide hydrochloride.

Examples of the base used in the reaction include organic bases such as triethylamine, pyridine, N,N-diethylaniline, 4-dimethylaminopyridine and diisopropylethylamine.

Examples of the solvent used in the reaction hydrocarbons such as benzene, toluene and hexane; ethers such as diethylether and tetrahydrofuran; halogenated hydrocarbons such as chloroform, dichloromethane, 1,2-dichloroethane and chlorobenzene; a mixture of these solvents; and so on.

The reaction time of the reaction is usually within a range from 5 minutes to 72 hours.

The reaction temperature of the reaction is usually within a range from −20° C. to 100° C. (from −20° C. to a boiling point of a solvent in case the boiling point of the solvent to be used is lower than 100° C.), and preferably from −5° C. to 100° C. (from −5° C. to a boiling point of a solvent in case the boiling point of the solvent to be used is lower than 100° C.)

In the reaction, a molar ratio of the alcohol compound represented by formula (2) to the carboxylic acid compound represented by formula (3) or a reactive derivative thereof to be used can be arbitrarily set, and preferably an equimolar ratio or a ratio close thereto.

The condensing agent or base can be usually used in an arbitrary proportion within a range from 0.25 mol to an excessive amount, and preferably from 1.0 mol to 2 mol, based on 1 mol of the alcohol compound represented by formula (2). These condensing agents or bases are appropriately selected according to the kind of the carboxylic acid compound represented by formula (3) or a reactive derivative thereof.

After the completion of the reaction, the reaction mixture is usually subjected to a post-treatment operation, for example, the reaction mixture is filtered and then the filtrate is concentrated, or the reaction mixture is poured into water and the obtained solution is extracted with an organic solvent and then concentrated, and thus the compound of the present invention can be obtained. The obtained compound of the present invention can be purified by an operation such as chromatography.

(Production Process 2)

Among the compound of the present invention, a compound represented by formula (1-1) in which a relative configuration of the substituent at the 1-position of the cyclopropane ring and the substituent at the 3-position of the cyclopropane ring is a cis configuration can be produced by the process shown below.

Formula (1-1)

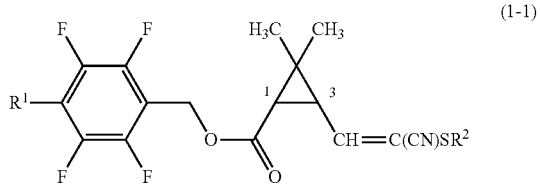

wherein $R^1$ and $R^2$ represents the same meanings as described above.

A process of reacting a lactone compound represented by formula (4):

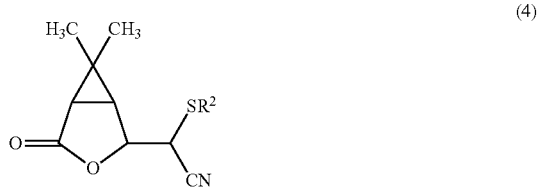

wherein $R^2$ represents the same meanings as described above, with a compound represented by formula (5)

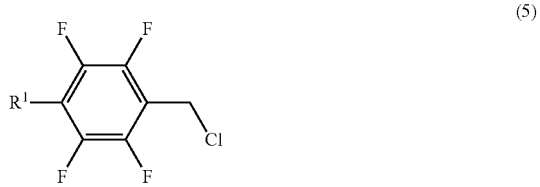

wherein $R^1$ represents the same meanings as described above, in the presence of a base.

The reaction is usually conducted in a solvent in the presence of a base. Examples of the solvent used in the reaction include ketones such as acetone, methyl ethyl ketone and methyl isobutyl ketone; ethers such as tetrahydrofuran; halogenated hydrocarbons such as chloroform, dichloromethane, 1,2-dichloroethane and chlorobenzene; acid amides such as N,N-dimethylformamide; sulfoxides such as dimethyl sulfoxide; a mixture of these solvents; and so on.

Examples of the base used in the reaction include carbonates such as sodium carbonate, potassium carbonate and cesium carbonate.

The reaction time of the reaction is usually within a range from 5 minutes to 72 hours.

The reaction temperature of the reaction is usually within a range from −20° C. to 100° C. (from −20° C. to a boiling point of a solvent in case the boiling point of the solvent to be used is lower than 100° C.), and preferably from −5° C. to 100° C. (from −5° C. to a boiling point of a solvent in case the boiling point of the solvent to be used is lower than 100° C.)

In the reaction, a molar ratio of the lactone compound represented by formula (4) to the compound represented by formula (4) to be used can be arbitrarily set, and preferably an equimolar ratio or a ratio close thereto.

The base can be usually used in an arbitrary proportion within a range from 1.00 mol to an excessive amount, and preferably from 1.0 mol to 2 mol, based on 1 mol of the lactone compound represented by formula (5).

After the completion of the reaction, the reaction mixture is usually subjected to a post-treatment operation, for example, the reaction mixture is filtered and then the filtrate is concentrated, or the reaction mixture is poured into water and the obtained solution is extracted with an organic solvent and then concentrated, and thus the compound represented by formula (1-1) can be isolated. The compound represented by formula (1-1) can be purified by an operation such as chromatography.

An alcohol compound represented by formula (2) is a compound described in JP-A-2000-63329 or JP-A-2001-213848.

An intermediate of the present invention can be produced, for example, by the process shown below.
(Reference Production Process 1)

Among the carboxylic acid compound represented by formula (3), a carboxylic acid compound represented by formula (3-1) in which a relative configuration of the substituent at the 1-position of the cyclopropane ring and the substituent at the 3-position of the cyclopropane ring is a trans configuration can be produced, for example, by the process shown below.
(First Step)

A caronaldehyde ester derivative represented by formula (6):

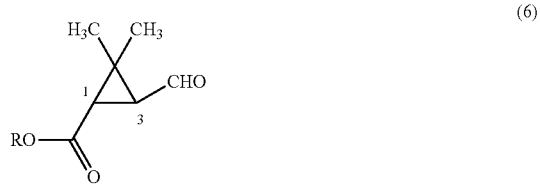
(6)

wherein R represents $C_1$-$C_5$ alkyl, is reacted with a nitrile compound represented by formula (7):

(7)

wherein $R^2$ represents the same meanings as described above, in the presence of a base, and thus a compound represented by formula (8):

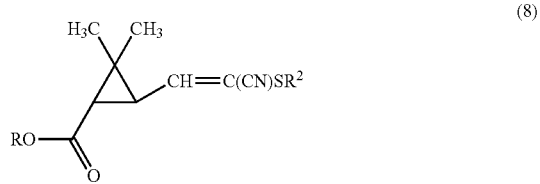
(8)

wherein R and $R^2$ represents the same meanings as described above, can be produced.
(Second Step)

The compound represented by formula (8) is subjected to a hydrolysis reaction in the presence of a base, and thus a carboxylic acid compound represented by formula (3-1):

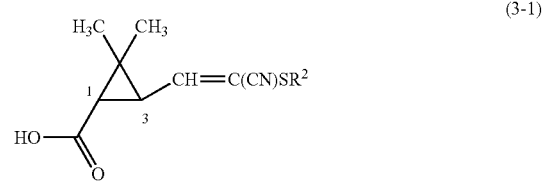
(3-1)

wherein $R^2$ represents the same meanings as described above, can be produced.

The reaction of the first step is usually conducted by using the nitrile compound represented by formula (7) in the proportion of 1.0 to 1.5 mol and a base in the proportion of 1 to 10 mol, based on 1 mol of the caronaldehyde ester derivative represented by formula (6), and reacting them in a polar solvent at 0° C. to 80° C., and preferably 0° C. to 30° C. Examples of the based used in the reaction include carbonates such as potassium carbonate and sodium carbonate; and alkali metal compounds such as sodium hydride. Examples of the polar solvent used in the reaction include acid amides such as N,N-dimethylformamide; and sulfoxides such as dimethyl sulfoxide.

After the completion of the reaction, the reaction mixture is usually subjected to a post-treatment operation, for example, the reaction mixture is added to water and the obtained solution is extracted with an organic solvent, and then the organic layer is dried and concentrated, and thus the compound represented by formula (8) can be obtained.

The reaction of the second step is usually conducted by using an alkali hydroxide in the proportion of 1 to 10 mol based on 1 mol of the compound represented by formula (8) in a solvent at 0° C. to 80° C., and preferably 0° C. to 30° C. Examples of the alkali hydroxide used in the reaction include potassium hydroxide and sodium hydride. Examples of the solvent used in the reaction include water and alcohols such as methanol and ethanol.

After the completion of the reaction, the reaction mixture is subjected to a post-treatment operation, for example, the reaction mixture is acidified and then extracted with an organic solvent, and then the organic layer is dried and concentrated, and thus the carboxylic acid compound represented by formula (3-1) can be isolated.

The caronaldehyde ester derivative represented by formula (6) is a compound described in Tetrahedron 45, 3039-3052 (1989).
(Reference Production Process 2)

A lactone compound represented by formula (4):

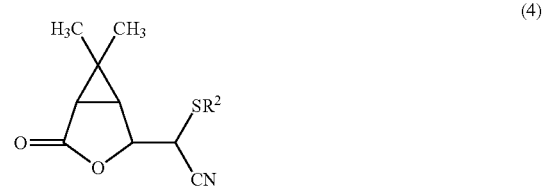
(4)

wherein $R^2$ represents the same meanings as described above, can be produced, for example, by reacting a lactol derivative represented by formula (9):

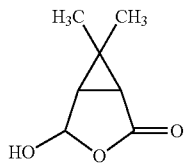 (9)

with a nitrile compound represented by formula (7):

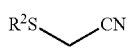 (7)

wherein $R^2$ represents the same meanings as described above, in the presence of a base.

The reaction is usually conducted by using the nitrile compound represented by formula (7) in the proportion of 1.0 to 1.5 mol and the base in the proportion of 1 to 10 mol, based on 1 mol of the lactol derivative represented by formula (9) in a polar solvent at 0° C. to 80° C., and preferably 0° C. to 50° C. Examples of the based used in the reaction include carbonates such as potassium carbonate and sodium carbonate; and alkali metal compounds such as sodium hydride. Examples of the polar solvent used in the reaction include the reaction include acid amides such as N,N-dimethylformamide; and sulfoxides such as dimethyl sulfoxide.

After the completion of the reaction, the reaction mixture is subjected to a post-treatment operation, for example, the reaction mixture is acidified and extracted with an organic solvent, and then the organic layer is dried and concentrated, and thus the lactone compound represented by formula (4) can be isolated.

The lactol derivative represented by formula (9) is a compound described in Synthetic Communications, 17, 1089-1094(1987).

Examples of pests on which the compound of the present invention has a control effect include harmful arthropod pests such as harmful insects and harmful acarines, and more specifically, the following pests.

Hemiptera: planthoppers such as *Laodelphax striatellus*, *Nilaparvata lugens*, and *Sogatella furcifera*, leafhoppers such as *Nephotettix cincticeps*, and *Nephotettix virescens*, aphids such as *Aphis gossypii*, and *Myzus persicae*, plant bugs such as *Nezara antennata*, *Riptortus clavetus*, *Eysarcoris lewisi*, *Eysarcoris parvus*, *Plautia stali*, and *Halyomorpha mista*, white flies such as *Trialeurodes vaporariorum*, *Bemisia tabaci*, and *Bemisia argentifolii*, scales such as *Aonidiella aurantii*, *Comstockaspis perniciosa*, *Unaspis citri*, *Ceroplastes rubens*, and *Icerya purchasi*, lace bugs, bed bugs such as *Cimex lectularius*, jumping plantlice and so on;

Lepidoptera: Pyralidae such as *Chilo suppressalis*, *Cnaphalocrocis medinalis*, *Notarcha derogata*, and *Plodia interpunctella*, *Spodoptera litura*, *Pseudaletia separata*, Noctuidae such as *Trichoplusia* spp., *Heliothis* spp., and *Earias* spp., Pieridae such as *Pieris rapae*, Tortricidae such as *Adoxopheys* spp., *Grapholita molesta*, *Adoxophyes orana fasciata*, and *Cydia pomonella*, Carposinidae such as *Carposina niponensis*, Lyonetiidae such as *Lyonetia* spp., Lymantriidae such as *Lymantria* spp., Lymantriidae such as *Euproctis* spp., Yponameutidae such as *Plutella xylostella*, Gelechiidae such as *Pectinophora gossypiella*, Arctiidae such as *Hyphantria cunea*, Tineidae such as *Tinea translucens*, and *Tineola bisselliella*, and so on;

Diptera: *Culex* spp. such as *Culex pipiens pallens*, *Culex tritaeniorhynchus*, and *Culex quinquefasciatus*, *Aedes* spp. such as *Aedes aegypti*, and *Aedes albopictus*, *Anopheles* spp. such as *Anopheles sinensis*, and *Anopheles gambiae*, Chironomidae, Muscidae such as *Musca domestica*, and *Muscina stabulans*, Calliphoridae, Sarcophagidae, little housefly, Anthomyiidae such as *Delia platura*, and *Delia antiqua*, Tephritidae, Drosophilidae, Phoridae such as *Megaselia spiracularis*, *Clogmia albipunctata*, Psychodidae, Simuliidae, Tabanidae, Stomoxyidae, Agromyzidae, and so on;

Coleoptera: *Diabrotica* spp. such as *Diabrotica virgifera virgifera*, and *Diabrotica undecimpunctata howardi*, Scarabaeidae such as *Anomala cuprea*, and *Anomala rufocuprea*, Curculionidae such as *Sitophilus zeamais*, *Lissorhoptrus oryzophilus*, and *Callosobruchuys chienensis*, Tenebrionidae such as *Tenebrio molitor*, and *Tribolium castaneum*, Chrysomelidae such as *Oulema oryzae*, *Aulacophora femoralis*, *Phyllotreta striolata*, and *Leptinotarsa decemlineata*, Dermestidae such as *Dermestes maculates*, Anobiidae, *Epilachna* spp. such as *Epilachna vigintioctopunctata*, Lyctidae, Bostrychidae, Ptinidae, Cerambycidae, *Paederus fuscipes*, and so on;

Blattodea: *Blattella germanica*, *Periplaneta fuliginosa*, *Periplaneta americana*, *Periplaneta brunnea*, *Blatta orientalis*, and so on;

Thysanoptera: *Thrips palmi*, *Thrips tabaci*, *Frankliniella occidentalis*, *Frankliniella intonsa*, and so on;

Hymenoptera: Formicidae such as *Monomorium pharaosis*, *Formica fusca japonica*, *Ochetellus glaber*, *Pristomyrmex pungens*, *Pheidole noda*, and *Linepithema humile*, long-legged wasps such as *Polistes chinensis antennalis*, *Polistes jadwigae*, and *Polistes rothneyi*, Vespidae such as *Vespa mandarinia japonica*, *Vespa simillima*, *Vespa analis insularis*, *Vespa crabro flavofasciata*, and *Vespa ducalis*, Bethylidae, *Xylocopa*, Pompilidae, Sphecoidae, mason wasp, and so on;

Orthoptera: mole crickets, grasshoppers, etc.;

Shiphonaptera: *Ctenocephalides felis*, *Ctenocephalides canis*, *Pulex irritans*, *Xenopsylla cheopis*, and so on;

Anoplura: *Pediculus humanus corporis*, *Phthirus pubis*, *Haematopinus eurysternus*, *Dalmalinia ovis*, and so on;

Isoptera: *Reticulitermes* spp. such as *Reticulitermes speratus*, *Coptotermes formosanus*, *Reticulitermes flavipes*, *Reticulitermes hesperus*, *Reticulitermes virginicus*, *Reticulitermes tibialis*, and *Heterotermes aureus*, *Incisitermes* spp. such as *Incisitermes* minor, and *Zootermopsis* spp. such as *Zootermopsis nevadensis*, and so on;

Acarina: Tetranychidae such as *Tetranychus urticae*, *Tetranychus kanzawai*, *Panonychus citri*, *Panonychus ulmi*, and *Oligonychus* spp., Eriophyidae such as *Aculops pelekassi*, and *Aculus schlechtendali*, Tarsonemidae such as *Polyphagotarsonemus latus*, Tenuipalpidae, Tuckerellidae, Ixodidae such as *Haemaphysalis longicornis*, *Haemaphysalis flava*, *Dermacentor variabilis*, *Ixodes ovatus*, *Ixodes persulcatus*), *Ixodes scapularis*, *Boophilus microplus*, *Amblyomma americanum*, and *Rhipicephalus sanguineus*, Acaridae such as *Tyrophagus putrescentiae*, Dermanyssidae such as *Dermatophagoides farinae*, *Dermatophagoides ptrenyssnus*, Cheyletidae such as *Cheyletus eruditus*, *Cheyletus malaccensis*, and *Cheyletus moorei*, chicken mite such as *Ornithonyssus bacoti*, *Ornithonyssus sylvairum*, and *Dermanyssus gallinae*, Trombiculidae such as *Leptotrombidium akamushi*, and so on;

Araneae: Japanese foliage spider (*Chiracanthium japonicum*), redback spider (*Latrodectus hasseltii*), *Nephila clavata* (Tetragnathidae), *Cyclosa octotuberculata*, St. Andrew's cross spider (*Argiope amoena*), Wasp sopider (*Argiope*

*bruennichii*), orb-weaving spider (*Araneus ventricosus*), grass spider (*Agelena silvatica*), wolf spider (*Pardosa astrigera*), dock spider (*Dolomedes sulfurous*), *Carrhotus xanthogramma*, common house spider (*Achaearanea tepidariorum*), *Coelotes insidiosus*, jumping spider (Salticidae), huntsman spider (*Heteropoda venatoria*), etc.;

*Chilopoda*: centipedes such as house centipede (*Thereuonema hilgendorfi*), *Scolopendra subspinipes*, *Scolopendra subspinipes japonica*, *Scolopocryptops rubiginosus*, *Bothropolys asperatus*, etc.;

*Diplopoda*: millipedes such as garden millipede (*Oxidus gracilis*), garden millipede (*Nedyopus tambanus*), train millipede (*Parafontaria laminate*), train millipede (*Parafontaria laminata armigera*), *Parafontaria acutidens*, *Epanerchodus orientalis*, etc.;

*Isopoda*: sow bugs such as *Porcellionides pruinosus* (Brandt), *Porcellio scaber Latreille*, pill bugs such as common pill bug (*Armadillidium vulgare*), sea louses such as wharf roach (*Ligia exotica*), etc.;

*Gastropoda*: tree slug (*Limax marginatus*), yellow slug (*Limax flavus*), etc.

The pest control agent of the present invention contains the compound of the present invention and an inert carrier. The pest control agent of the present invention is usually formed into formulations described below. Examples of the formulation include an oil solution, an emulsifiable concentrate, a wettable powder, a flowable formulation (e.g., an aqueous suspension, or an aqueous emulsion), a microcapsule, a dust, a granule, a tablet, an aerosol, a carbon dioxide formulation, a heat transpiration formulation (e.g., an insecticidal coil, an electric insecticidal mat, or a liquid absorbing core-type heat transpiration pesticide), a piezo insecticidal formulation, a heat fumigant (e.g., a self combustion-type fumigant, a chemical reaction-type fumigant, or a porous ceramic plate fumigant), an unheated transpiration formulation (e.g., a resin transpiration formulation, a paper transpiration formulation, an unwoven fabric transpiration formulation, a knit fabric transpiration formulation, or a sublimating tablet), an aerosol formulation (e.g., a fogging formulation), a direct contact formulation (e.g., a sheet-shaped contact formulation, a tape-shaped contact formulation, or a net-shaped contact formulation), an ULV formulation and a poison bait Examples of the method for formulation include the following methods.

(1) A method comprising mixing the compound of the present invention with a solid carrier, a liquid carrier, a gaseous carrier or a poison bait, followed by addition of a surfactant and other auxiliary agents for formulation, and if necessary, further processing.

(2) A method comprising impregnation of a base material containing no active ingredient with the compound of the present invention.

(3) A method comprising mixing the compound of the present invention and a base material, followed by subjecting the mixture to mold processing.

These formulations usually contain 0.001 to 98% by weight of the compound of the present invention, depending on formulation forms.

Examples of the solid carrier used in the formulation include fine powders or granules of clays (e.g., kaolin clay, diatomaceous earth, bentonite, Fubasami clay, or acid white clay), synthetic hydrated silicon oxide, talc, ceramics, other inorganic minerals (e.g., sericite, quartz, sulfur, active carbon, calcium carbonate, or hydrated silica) and fine powder and granulated substances such as chemical fertilizers (e.g., ammonium sulfate, ammonium phosphate, ammonium nitrate, ammonium chloride, or urea); substances that are solid at room temperature (e.g., 2,4,6-triisopropyl-1,3,5-trioxane, naphthalene, p-dichlorobenzene, or camphor, adamantine); as well as felt, fiber, fabric, knit, sheet, paper, thread, foam, porous material and multi-filament comprising one or more substances selected from the group consisting of wool, silk, cotton, hemp, pulp, synthetic resins (e.g., polyethylene resins such as low density polyethylene, straight chain low density polyethylene and high density polyethylene; ethylene-vinyl ester copolymers such as an ethylene-vinyl acetate copolymer; ethylene-methacrylate copolymers such as an ethylene-methyl methacrylate copolymer and an ethylene-ethyl methacrylate copolymer; ethylene-acrylate copolymers such as an ethylene-methyl acrylate copolymer and an ethylene-ethyl acrylate copolymer; ethylene-vinylcarboxylic acid copolymers such as an ethylene-acrylic acid copolymer; ethylene-tetracyclododecene copolymers; polypropylene resins such as a propylene homopolymer and a propylene-ethylene copolymer; poly-4-methylpentene-1, polybutene-1, polybutadiene, polystyrene; acrylonitrile-styrene resin; acrylonitrile-butadiene-styrene resins; styrene elastomers such as a styrene-conjugated diene block copolymer and a hydrogenated styrene-conjugated diene block copolymer; fluorine resins; acrylic resins such as methyl polymethacrylate; polyamide resins such as nylon 6 and nylon 66; polyester resins such as polyethylene terephthalate, polyethylene naphthalate, polybutylene terephthalate and polycyclohexylene dimethylene terephthalate; or porous resins such as polycarbonate, polyacetal, polyacryl sulfone, polyarylate, hydroxybenzoic acid polyester, polyetherimide, polyester carbonate, polyphenylene ether resins, polyvinyl chloride, polyvinylidene chloride, polyurethane, foamed polyurethane, foamed polypropylene and foamed ethylene), glass, metal and ceramics.

Examples of the liquid carrier include aromatic or aliphatic hydrocarbons (e.g., xylene, toluene, alkylnaphthalene, phenylxylylethane, kerosene, light oil, hexane, or cyclohexane), halogenated hydrocarbons (e.g., chlorobenzene, dichloromethane, dichloroethane, or trichloroethane), alcohols (e.g., methanol, ethanol, isopropyl alcohol, butanol, hexanol, benzyl alcohol, or ethylene glycol), ethers (e.g., diethyl ether, ethylene glycol dimethyl ether, diethylene glycol monomethyl ether, diethylene glycol monoethyl ether, propylene glycol monomethyl ether, tetrahydrofuran, or dioxane), esters (e.g., ethyl acetate, or butyl acetate), ketones (e.g., acetone, methyl ethyl ketone, methyl isobutyl ketone, or cyclohexanone), nitriles (e.g., acetonitrile, or isobutyronitrile), sulfoxides (e.g., dimethyl sulfoxide), acid amides (e.g., N,N-dimethylformamide, N,N-dimethylacetamide, or N-methylpyrrolidone), alkylidene carbonate (e.g., propylene carbonate), vegetable oils (e.g., soybean oil, or cottonseed oil), plant essential oils (e.g., orange oil, hyssop oil, or lemon oil), and water.

Examples of the gaseous carrier include butane gas, chlorofluorocarbon, liquefied petroleum gas (LPG), dimethyl ether and carbon dioxide.

Examples of the surfactant include alkyl sulfate, alkyl sulfonate, alkylaryl sulfonate, alkylaryl ethers, polyoxyethylenated alkylaryl ethers, polyethylene glycol ethers, polyhydric alcohol esters and sugar alcohol derivatives.

Examples of the other auxiliary agents for formulation include a binder, a dispersant and a stabilizer. Specifically, there are, for example, casein, gelatin, polysaccharides (e.g., starch, gum arabic, cellulose derivatives, or alginic acid), lignin derivatives, bentonite, saccharides, synthetic water-soluble polymers (e.g., polyvinyl alcohol, or polyvinyl pyrrolidone), polyacrylic acid, BHT (2,6-di-tert-butyl-4-methylphenol) and BHA (a mixture of 2-tert-butyl-4-methoxyphenol and 3-tert-butyl-4-methoxyphenol).

Examples of a base material for the insecticidal coil include a mixture of vegetable powder such as wood flour and lees powder, and a binder such as incense material powder, starch and gluten.

Examples of a base material for the electric insecticidal mat include a plate obtained by hardening cotton linter and a plate obtained by hardening fibrils of a mixture of cotton linter and pulp.

Examples of a base material for the self combustion-type fumigant include combustible exothermic agents such as nitrate, nitrite, guanidine salt, potassium chlorate, nitrocellulose, ethylcellulose and wood flour, thermal decomposition stimulants such as alkali metal salt, alkaline earth metal salt, dichromate and chromate, oxygen carriers such as potassium nitrate, combustion-supporting agents such as melamine and flour starch, extenders such as diatomaceous earth, and binders such as synthetic glue.

Examples of a base material for the chemical reaction-type fumigant include exothermic agents such as alkali metal sulfide, polysulfide, hydrosulfide and calcium oxide, catalytic agents such as a carbonaceous material, iron carbide and active white clay, organic foaming agents such as azodicarbonamide, benzenesulfonylhydrazide, dinitropentamethylenetetramine, polystyrene and polyurethane, and fillers such as strips of natural fiber and synthetic fiber.

Examples of a resin used as a base material of the resin transpiration formulation include polyethylene resins such as low density polyethylene, straight chain low density polyethylene and high density polyethylene; ethylene-vinyl ester copolymers such as an ethylene-vinyl acetate copolymer; ethylene-methacrylate copolymers such as an ethylene-methyl methacrylate copolymer and an ethylene-ethyl methacrylate copolymer; ethylene-acrylate copolymers such as an ethylene-methyl acrylate copolymer and an ethylene-ethyl acrylate copolymer; ethylene-vinylcarboxylic acid copolymers such as an ethylene-acrylic acid copolymer; ethylene-tetracyclododecene copolymers; polypropylene resins such as a propylene copolymer and a propylene-ethylene copolymer; poly-4-methylpentene-1, polybutene-1, polybutadiene, polystyrene, acrylonitrile-styrene resins; acrylonitrile-butadiene-styrene resins; styrene elastomers such as a styrene-conjugated diene block copolymer and a hydrogenated styrene-conjugated diene block copolymer; fluorine resins; acrylic resins such as methyl polymethacrylate; polyamide resins such as nylon 6 and nylon 66; polyester resins such as polyethylene terephthalate, polyethylene naphthalate, polybutylene butalate and polycyclohexylene dimethylene terephthalate; polycarbonate, polyacetal, polyacryl sulfone, polyarylate, hydroxybenzoic acid polyester, polyetherimide, polyester carbonate, polyphenylene ether resin, polyvinyl chloride, polyvinylidene chloride and polyurethane. These base materials may be used alone or as a combination of two or more kinds. If necessary, a plasticizer such as phthalate esters (e.g., dimethyl phthalate, dioctyl phthalate, etc.), adipic acid esters and stearic acid may be added to these base materials. The resin transpiration formulation can be prepared by mixing the compound of the present invention with the base material, kneading the mixture, followed by molding it by injection molding, extrusion molding or pressure molding. The resultant resin formulation can be subjected to further molding or cutting procedure, if necessary, to be processed into shapes such as a plate, film, tape, net or string shape. These resin formulations can be processed into animal collars, animal ear tags, sheet products, trap strings, gardening supports and other products.

Examples of a base material for the poison bait include bait ingredients such as grain powder, vegetable oil, saccharide and crystalline cellulose, antioxidants such as dibutylhydroxytoluene and nordihydroguaiaretic acid, preservatives such as dehydroacetic acid, accidental ingestion inhibitors for children and pets such as a chili powder; insect attraction fragrances such as cheese flavor, onion flavor and peanut oil.

The pest control method of the present invention usually conducted by applying an effective amount of the compound of the present invention to a pest or a habitat thereof (e.g. plant bodies, soil, the interior of a house, animal bodies, the interior of a car, or outdoor open space) in a form of a pest control agent of the present invention.

A method for applying the pest control agent of the present invention includes the following methods, and appropriately selected depending on the form of the pest control agent of the present invention, the application area and so on.

(1) A method comprising applying a pest control agent of the present invention as it is to a pest or a habitat of the pest.

(2) A method comprising diluting a pest control agent of the present invention with a solvent such as water, and then spraying the dilution to a pest or a habitat of the pest. In this method, the pest control agent of the present invention is usually formulated into an emulsifiable concentrate, a wettable powder, a flowable formulation, a microcapsule or the like. The formulation is usually diluted so that the concentration of the compound of the present invention can be 0.1 to 10,000 ppm.

(3) A method comprising heating a pest control agent of the present invention at a habitat of a pest, thereby allowing an active ingredient to volatilize and diffuse from the pest control agent.

In this case, any of the amount and concentration of application of the compound of the present invention can be appropriately determined depending on the form, application period, application area, application method, kind of a pest, damage to be incurred and so on.

When the compound of the present invention is used for prevention of epidemics, the amount to be applied is usually from 0.0001 to 1,000 mg/m$^3$ of the compound of the present invention in the case of applying to a space, and from 0.0001 to 1,000 mg/m$^2$ of the compound of the present invention in the case of applying to a plane. An insecticidal coil or an electric insecticidal mat is applied by heating to volatilize and diffuse an active ingredient, depending on the form of the formulation. A resin transpiration formulation, a paper transpiration formulation, an unwoven fabric transpiration formulation, a knit fabric transpiration formulation or a sublimating tablet are allowed to stand as it is in a space to be applied, and placed under air blowing.

When the pest control agent of the present invention is applied to a space for the purpose of prevention of epidemics, examples of the space include a closet, a Japanese cabinet, a Japanese chest, a cupboard, a toilet, a bathroom, a shed, a living room, a dining room, a garage, the interior of a car and so on. The pest control agent can be also applied to outdoor open space.

When the pest control agent of the present invention is used for controlling external parasites of livestock such as cows, horses, pigs, sheep, goats and chickens and small animals such as dogs, cats, rats and mice, the pest control agent of the present invention can be applied to the animals by a known method in the veterinary field. Specifically, when systemic control is intended, the pest control agent of the present invention is administered to the animals as a tablet, a mixture with feed or a suppository, or by injection (including intramuscular, subcutaneous, intravenous and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin transpiration formulation to the animal. In the case of administering to an animal body, the dosage of the compound of the present invention is usually in the range from 0.1 to 1,000 mg per 1 kg of an animal body weight.

When the pest control agent of the present invention is used for controlling a pest in the agricultural field, the amount can widely vary depending on the application period, application area, application method and other factors, and is usually in the range from 1 to 10,000 g in terms of the compound of the present invention per 10,000 m$^2$. When the pest control agent of the present invention is formulated into an emulsifiable concentrate, a wettable powder, a flowable formulation and so on, the pest control agent is usually applied after diluting with water so that the concentration of the active ingredient becomes 0.01 to 10,000 ppm, and a granule or a dust is usually applied as it is.

These formulations or water dilutions of the formulations may be directly sprayed over pests or plants such as crop plants to be protected from pests, or may be used in the soil treatment for the control of pests which inhabit the soil of the cultivated land.

Application can also be conducted by a method of directly winding the resin formulation formed into sheet-shaped, or string- or cord-shaped formulation around plants, disposing the formulation in the neighborhood of plants, or spreading the formulation on the soil surface at the root.

The compound of the present invention can be used as a pest control agent in cultivating field such as farm, paddy field, lawn or orchard, or non-cultivating field. The compound of the present invention can control pests inhabiting the cultivating field in the cultivating field where the following "plant crops" are cultivated.

Agricultural crops: corn, rice, wheat, barley, rye, oat, sorghum, cotton, soybean, peanut, sarrazin, sugar beet, rapeseed, sunflower, sugar cane, tobacco, etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid, etc.;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date, coconut palm, oil palm, etc.;

Trees other than fruit trees: tea, mulberry, woody plants (azalea, camellia, hydrangea, sasanqua, *Illicium religiosum*, cherry tree, tulip tree, crape myrtle, fragrant olive etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse-chestnut etc.), sweet viburnum, *Podocarpus macrophyllus*, Japanese cedar, Japanese cypress, croton, spindle tree, Chainese howthorn, etc.

Lawn: zoysia (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.;

Others: flowers (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, verbena, cymbidium, begonia, etc.), bio-fuel plants (Jatropha, safflower, gold-of-pleasure, switchgrass, Miscanthus, ribbon grass, giant reed, kenaf, cassava, willow, etc.), foliage plant; etc.

The above "plant crops" include gene transgenic plant crops.

The compound of the present invention can be mixed with or can be used in combination with other insecticide, acaricide, nematocide, soil pest control agent, fungicide, herbicide, plant growth regulating agent, repellent, synergist, fertilizer, or soil modifier.

Examples of active ingredient of such the insecticide and acaricide include:

(1) Synthetic Pyrethroid Compounds:

acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl=2,2-dimethyl-3-(1-propenyl)cyclopropane carboxylate, 2,3,5,6-tetrafluoro-4-(methoxymethyl)benzyl=2,2-dimethyl-3-(2-methyl-1-propenyl)cyclopropane carboxylate, 2,3,5,6-tetrafluoro-4-(methoxymethyl)benzyl=2,2,3,3-tetramethylcyclopropane carboxylate, and so on;

(2) Organic Phosphorous Compounds:

acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion:ECP, dichlorvos:DDVP, dimethoate, dimethylvinphos, disulfoton, EPN, ethion, ethoprophos, etrimfos, fenthion:MPP, fenitrothion:MEP, fosthiazate, formothion, Hydrogen phosphide, isofenphos, isoxathion, malathion, mesulfenfos, methidathion:DMTP, monocrotophos, naled:BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, vamidothion, phorate, cadusafos, and so on;

(3) Carbamate Compounds:

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, xylylcarb, aldicarb, and so on;

(4) Nereistoxin Compounds:
cartap, bensultap, thiocyclam, monosultap, bisultap, and so on;

(5) Neonicotinoid Compounds:
imidacloprid, nitenpyram, acetamiprid, thiamethoxam, thiacloprid, dinotefuran, clothianidin, and so on;

(6) Benzoylurea Compounds:
chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, and so on;

(7) Phenylpyrazole Compounds:
acetoprole, ethiprole, fipronil, vaniliprole, pyriprole, pyrafluprole, and so on;

(8) Bt Toxin Insecticides:
Live spores derived from and crystal toxins produced from *Bacillus thuringiesis* and a mixture thereof;

(9) Hydrazine Compounds:
chromafenozide, halofenozide, methoxyfenozide, tebufenozide, and so on;

(10) Organic Chlorine Compound:
aldrin, dieldrin, dienochlor, endosulfan, methoxychlor, and so on;

(11) Natural Insecticides:
machine oil, nicotine-sulfate;

(12) Other Insecticides:
avermectin-B, bromopropylate, buprofezin, chlorphenapyr, cyromazine, D-D(1, 3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, Sulfur, metaflumizone, spirotetramat, pyrifluquinazone, spinetoram, chlorantraniliprole, tralopyril, and so on.

Examples of the active ingredient of the repellent include N,N-diethyl-m-toluamide, limonene, linalool, citronellal, menthol, menthone, hinokitiol, geraniol, eucalyptol, indoxacarb, carane-3,4-diol, MGK-R-326, MGK-R-874 and BAY-KBR-3023.

Examples of the active ingredient of the synergist include 5-[2-(2-butoxyethoxy)ethoxymethyl]-6-propyl-1,3-benzodioxol, N-(2-ethylhexyl)bicyclo[2.2.1]hept-5-ene-2,3-dicarboxyimide, octachlorodipropylether, thiocyanoacetic acidisobornyl, N-(2-ethylhexyl)-1-isopropyl-4-methylbicyclo[2.2.2]oct-5-ene-2,3-dicarboxyimide.

EXAMPLES

The present invention will be further described in more detail below by way of Production Examples, Reference Production Examples, Formulation Examples and Test Examples, but the present invention is not limited to these Examples.

First, Production Examples of the compound of the present invention are shown below. In $^1$H-NMR, the description "1.21+1.22 (s+s, 3H)" means that peaks of singlet(s) exist at 1.21 ppm and 1.22 ppm, and the total of integral values of these two peaks is 3H, for example.

Production Example 1

4-methoxymethyl-2,3,5,6-tetrafluorobenzyl alcohol (0.70 g, 3.13 mmol) and 0.7 mL of pyridine were added to 10 mL of toluene, and a toluene solution (5 mL) of (1R)-trans-3-[(1EZ)-2-cyano-2-(methylthio)ethenyl]-2,2-dimethylcyclopropanecarboxylic acid chloride (0.71 g, 3.10 mmol) was added thereto. After stirring the mixture at room temperature for 12 hours, the reaction solution was poured into 5 mL of 5% hydrochloric acid and 30 mL of ice water and the solution was extracted with ethyl acetate. The organic layer was washed with 20 mL of saturated brine and 5 mL of saturated sodium bicarbonate water respectively, and then dried over magnesium sulfate. After concentration of the organic layer under reduced pressure, the residue was subjected to silica gel chromatography to obtain 0.43 g of 4-methoxymethyl-2,3,5,6-tetrafluorobenzyl=(1R)-trans-3-[(1E)-2-cyano-2-(methylthio)ethenyl]-2,2-dimethylcyclopropane carboxylate (hereinafter referred to as the compound of the present invention (1)) represented by the following formula:

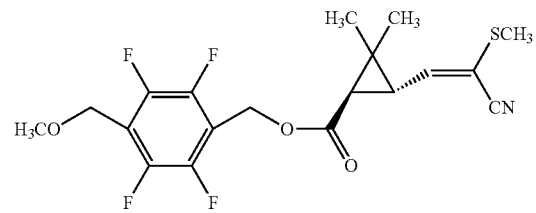 [SMILES: COCc1c(F)c(F)c(COC(=O)[C@@H]2[C@@H](/C=C(\C#N)SC)C2(C)C)c(F)c1F]

as a fraction having higher polarity.

Pale yellow liquid: $^1$H-NMR(CDCl$_3$,TMS) δ (ppm): 1.23 (s, 3H), 1.33 (s, 3H), 1.80 (d, 1H), 2.40 (s, 3H), 2.52 (dd, 1H), 3.41 (s, 3H), 4.59 (s, 2H), 5.26 (s, 2H), 6.15 (d, 1H)

Production Example 2

The operation was conducted in the same manner as Production Example 1, except that (1R)-trans-3-[(1EZ)-2-cyano-2-(butylthio)ethenyl]-2,2-dimethylcyclopropanecarboxylic acid chloride was used in place of (1R)-trans-3-[(1EZ)-2-cyano-2-(methylthio)ethenyl]-2,2-dimethylcyclopropanecarboxylic acid chloride, 4-methoxymethyl-2,3,5,6-tetrafluorobenzyl=(1R)-trans-3-[(1EZ)-2-cyano-2-(butylthio)ethenyl]-2,2-dimethylcyclopropane carboxylate (E:Z=50:50) (hereinafter referred to as the compound of the present invention (2)) represented by the following formula was obtained.

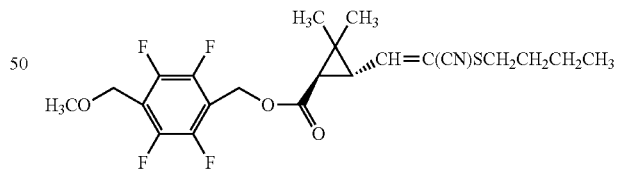

Colorless liquid: $^1$H-NMR(CDCl$_3$,TMS) δ (ppm):0.91-0.95 (m, 3H), 1.22 (s, 1.5H), 1.23 (s, 1.5H), 1.33 (s, 1.5H), 1.36 (s, 1.5H), 1.41-1.62 (m, 4H), 1.77 (d, 0.5H), 1.81 (d, 0.5H), 2.51-2.56 (m, 1H), 2.79 (m, 1H), 2.81 (m, 1H), 3.41 (s, 3H), 4.59 (s, 2H), 5.26 (s, 2H), 6.20 (d, 0.5H), 6.24 (d, 0.5H)

Production Example 3

The operation was conducted in the same manner as Production Example 1, except that (1R)-trans-3-[(1EZ)-2-cyano-2-(ethylthio)ethenyl]-2,2-dimethylcyclopropanecarboxylic acid chloride was used in place of (1R)-trans-3-

[(1EZ)-2-cyano-2-(methylthio)ethenyl]-2,2-dimethylcyclopropanecarboxylic acid chloride, 4-methoxymethyl-2,3,5,6-tetrafluorobenzyl=(1R)-trans-3-[(1EZ)-2-cyano-2-(ethylthio)ethenyl]-2,2-dimethylcyclopropane carboxylate (E:Z=50:50) (hereinafter referred to as the compound of the present invention (3)) represented by the following formula was obtained.

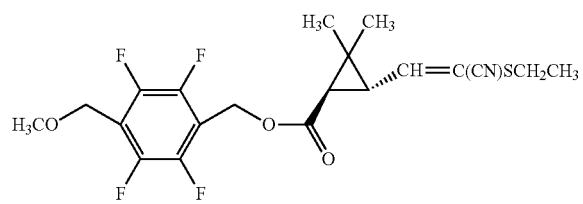

Colorless liquid: $^1$H-NMR(CDCl$_3$,TMS) δ (ppm):1.22-1.34 (m, 9H), 1.79 (d, 0.5H), 1.82 (d, 0.5H), 2.52-2.56 (m, 1H), 2.84 (q, 1H), 2.93 (q, 1H), 3.41 (s, 3H), 4.59 (s, 2H), 5.26 (s, 2H), 6.22 (d, 0.5H), 6.27 (d, 0.5H)

Production Example 4

4-methoxymethyl-2,3,5,6-tetrafluorobenzyl=(1R)-trans-3-[(1EZ)-2-cyano-2-(ethylthio)ethenyl]-2,2-dimethylcyclopropanecarboxylate (E:Z=50:50) obtained in Production Example 3 was subjected to silica gel column chromatography again to obtain, as a fraction having higher polarity, 4-methoxymethyl-2,3,5,6-tetrafluorobenzyl=(1R)-trans-3-[(1EZ)-2-cyano-2-(ethylthio)ethenyl]-2,2-dimethylcyclopropane carboxylate (E:Z=90:10) (hereinafter referred to as the compound of the present invention (4), represented by the following formula:

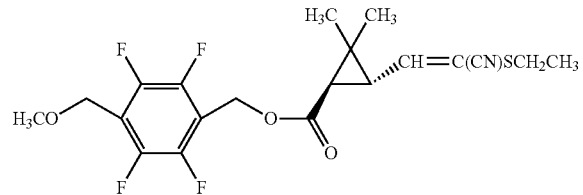

was obtained.

Production Example 5

The operation was conducted in the same manner as Production Example 3, except that 4-methyl-2,3,5,6-tetrafluorobenzyl alcohol was used in place of 4-methoxymethyl-2,3,5,6-tetrafluorobenzyl alcohol, 4-methyl-2,3,5,6-tetrafluorobenzyl=(1R)-trans-3-[(1EZ)-2-cyano-2-(ethylthio)ethenyl]-2,2-dimethylcyclopropane carboxylate (E:Z=90:10) (hereinafter referred to as the compound of the present invention (5)) represented by the following formula was obtained.

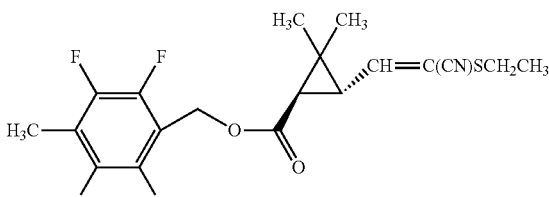

Colorless liquid: $^1$H-NMR(CDCl$_3$,TMS) δ (ppm):1.22-1.34 (m, 9H), 1.79 (d, 0.1H), 1.81 (d, 0.9H), 2.29 (m, 3H), 2.51-2.55 (m, 1H), 2.84-2.88 (m, 2H), 5.23 (s, 2H), 6.22 (d, 0.9H), 6.27 (d, 0.1H)

With respect to the production of the carboxylic acid compound (4) or the like, Reference Production Examples are shown below.

Reference Production Example 1

Methyl=(1R)-trans-3-formyl-2,2-dimethylcyclopropane carboxylate (6.41 g, 41.1 mmol), methylthioacetonitrile (3.94 g, 45.2 mmol) and potassium carbonate (6.24 g, 45.2 mmol) were added to a mixture of N,N-dimethylformamide (40 mL) and toluene (15 mL), followed by stirring it at 100° C. for 3 hours. The reaction mixture cooled to room temperature was added to 200 ml of ice water, and the solution was extracted twice with ethyl acetate (100 mL each). The obtained ethyl acetate layers were combined, washed once with saturated brine (50 mL) and then dried over magnesium sulfate. After concentration of the organic layer under reduced pressure, the residue was subjected to silica gel chromatography to obtain 8.23 g of methyl=(1R)-trans-3-[(1EZ)-2-cyano-2-(methylthio)ethenyl]-2,2-dimethylcyclopropane carboxylate represented by the following formula:

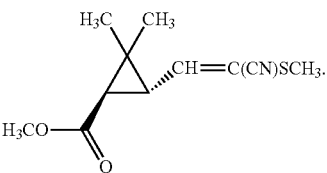

Colorless liquid: $^1$H-NMR(CDCl$_3$, TMS) δ (ppm): 1.23+1.24 (s+s, 3H), 1.32+1.33 (s+s, 3H), 1.79+1.80 (d+d, 1H, J=5.2 Hz), 2.40+2.46 (s+s, 3H), 2.50 to 2.53 (m, 1H), 3.70 (s, 3H), 6.18+6.21 (d+d, 1H, J=10.0 Hz)

Reference Production Example 2

Methyl=(1R)-trans-3-[(1EZ)-2-cyano-2-(methylthio)ethenyl]-2,2-dimethylcyclopropane carboxylate (2.29 g, 10.2 mmol) was dissolved in a mixture of methanol (6 mL) and water (10 mL), and potassium hydroxide (1.1 g, 19.6 mmol) was added thereto, followed by stirring it at room temperature for 12 hours. The reaction mixture was added to ice water (30 mL), and the solution was extracted with ethyl acetate (20 mL). To the obtained aqueous layer, hydrochloric acid was added until the pH became 2, followed by extraction twice with ethyl acetate (30 mL). The obtained ethyl acetate layers were combined, washed twice with saturated brine (30 mL) and then dried over magnesium sulfate. After concentration of the organic layer under reduced pressure, 2.08 g of (1R)-trans-3-[(1EZ)-2-cyano-2-(methylthio)ethenyl]-2,2-dimethylcyclopropanecarboxylic acid represented by the following formula:

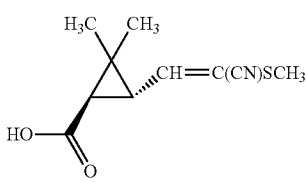

was obtained.

Pale yellow crystal: $^1$H-NMR(CDCl$_3$, TMS) δ (ppm): 1.24+1.25 (s+s, 3H), 1.36+1.37 (s+s, 3H), 1.79+1.81 (d+d, 1H, J=5.2 Hz), 2.41+2.47 (s+s, 3H), 2.50 to 2.56 (m, 1H), 6.17+6.21 (d+d, 1H,E+Z, J=10.4 Hz)

Reference Production Example 3

Chloroacetonitrile (4.0 g, 53.0 mmol) and potassium carbonate (8.8 g, 63.8 mmol) were added to N,N-dimethylformamide (30 mL) and ethyl mercaptan (3.7 mL, 49.9 mmol) was added thereto under ice cooling, followed by stirring it at room temperature for 24 hours. Thereafter, methyl=(1R)-trans-3-formyl-2,2-dimethylcyclopropane carboxylate (8.20 g, 52.6 mmol) and potassium carbonate (9.0 g, 65.2 mmol) were added, followed by further stirring it at room temperature for 24 hours. The reaction mixture was added to ice water (100 mL), and the solution was extracted twice with ethyl acetate (100 mL each). The obtained ethyl acetate layers were combined, washed once with saturated brine (50 mL) and then dried over magnesium sulfate. After concentration of the organic layer under reduced pressure, the residue was subjected to silica gel chromatography to obtain 9.93 g of methyl=(1R)-trans-3-[(1EZ)-2-cyano-2-(ethylthio)ethenyl]-2,2-dimethylcyclopropane carboxylate represented by the following formula:

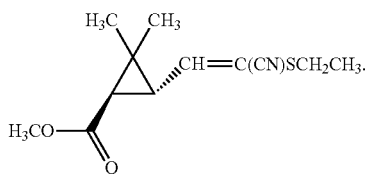

Colorless liquid: $^1$H-NMR(CDCl$_3$, TMS) δ (ppm): 1.23+1.24 (s+s, 3H), 1.26 to 1.33 (m, 3H), 1.33+1.35 (s+s, 3H), 1.79 to 1.83 (m, 1H), 2.50 to 2.55 (m, 1H), 2.84 to 2.90 (m, 2H), 3.71 (s, 3H), 6.25 to 6.29 (m, 1H)

Reference Production Example 4

After dissolving methyl=(1R)-trans-3-[(1EZ)-2-cyano-2-(ethylthio)ethenyl]-2,2-dimethylcyclopropane carboxylate (9.90 g, 41.4 mmol) in a mixture of methanol (15 mL) and water (5 mL), potassium hydroxide (3.5 g, 62.5 mmol) was added thereto, followed by stirring it at room temperature for 12 hours. The reaction mixture was added to ice water (60 mL), and the solution was extracted with ethyl acetate (50 mL) To the obtained aqueous layer, 5% aqueous hydrochloric acid solution was added until the pH became 2, followed by extraction twice with ethyl acetate (50 mL). The obtained ethyl acetate layers were combined, washed twice with saturated brine (50 mL) and then dried over magnesium sulfate. After concentration of the organic layer under reduced pressure, 8.98 g of (1R)-trans-3-[(1EZ)-2-cyano-2-(ethylthio)ethenyl]-2,2-dimethylcyclopropanecarboxylic acid represented by the following formula:

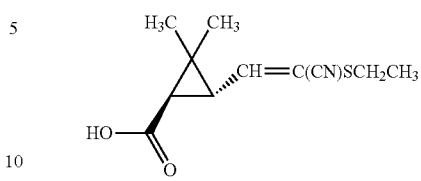

was obtained.

Reference Production Example 5

To methyl=(1R)-trans-3-[(1EZ)-2-cyano-2-(ethylthio)ethenyl]-2,2-dimethylcyclopropanecarboxylic acid (8.98 g, 39.9 mmol), toluene (25 mL) was added and then thionyl chloride (5.0 g, 42.0 mmol) was added. Furthermore, N,N-dimethylformamide (50 mg) was added, followed by stirring at an inner temperature of 60 to 70° C. for 4 hours. The reaction mixture was concentrated under reduced pressure to obtain 9.62 g of (1R)-trans-3-[(1EZ)-2-cyano-2-(ethylthio)ethenyl]-2,2-dimethylcyclopropanecarboxylic acid chloride represented by the following formula:

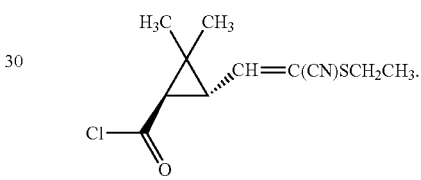

Reference Production Example 6

The reaction was conducted in the same manner as Reference Production Example 3, except that propyl mercaptan was used in place of ethyl mercaptan, methyl=(1R)-trans-3-[(1EZ)-2-cyano-2-(propylthio)ethenyl]-2,2-dimethylcyclopropane carboxylate represented by the following formula:

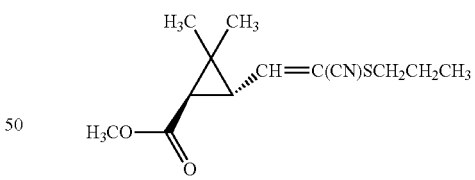

was obtained

Colorless liquid: $^1$H-NMR(CDCl$_3$, TMS) δ (ppm): 0.99 to 1.00 (m, 3H), 1.23+1.24 (s+s, 3H), 1.33+1.35 (s+s, 3H), 1.62 to 1.70 (m, 2H), 1.79 to 1.82 (m, 1H), 2.50 to 2.56 (m, 1H), 2.80 to 2.89 (m, 2H), 3.71 (s, 3H), 6.23 to 6.28 (m, 1H)

Reference Production Example 7

The reaction was conducted in the same manner as Reference Production Example 4, except that methyl=(1R)-trans-3-[(1EZ)-2-cyano-2-(propylthio)ethenyl]-2,2-dimethylcyclopropane carboxylate was used in place of methyl=(1R)-trans-3-[(1EZ)-2-cyano-2-(ethylthio)ethenyl]-2,2-dimethylcyclopropane carboxylate, (1R)-trans-3-[(1EZ)-2- cyano-2-(propylthio)ethenyl]-2,2-dimethylcyclopropanecarboxylic acid represented by the following formula:

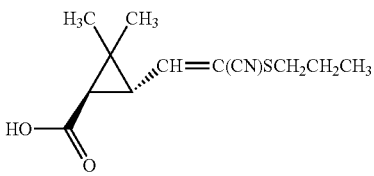

was obtained.

Pale yellow solid: $^1$H-NMR(CDCl$_3$, TMS) δ (ppm): 0.99 to 1.04 (m, 3H), 1.25+1.26 (s+s, 3H), 1.36+1.37 (s+s, 3H), 1.62 to 1.70 (m, 2H), 1.79 to 1.83 (m, 1H), 2.53 to 2.56 (m, 1H), 2.80 to 2.90 (m, 2H), 6.23 to 6.28 (m, 1H)

Reference Production Example 8

The reaction was conducted in the same manner as Reference Production Example 3, except that butyl mercaptan was used in place of ethyl mercaptan, methyl=(1R)-trans-3-[(1EZ)-2-cyano-2-(butylthio)ethenyl]-2,2-dimethylcyclopropane carboxylate represented by the following formula:

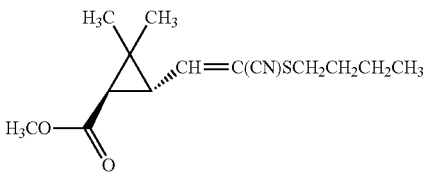

was obtained.

Colorless liquid: $^1$H-NMR(CDCl$_3$, TMS) δ (ppm): 0.92 to 0.95 (m, 3H), 1.22+1.23 (s+s, 3H), 1.32+1.33 (s+s, 3H, 1.41 to 1.65 (m, 4H), 1.79 to 1.82 (m, 1H), 2.52 to 2.56 (m, 1H), 2.80 to 2.91 (m, 2H), 3.71 (s, 3H), 6.22 to 6.28 (m, 1H)

Reference Production Example 9

The reaction was conducted in the same manner as Reference Production Example 4, except that methyl=(1R)-trans-3-[(1EZ)-2-cyano-2-(butylthio)ethenyl]-2,2-dimethylcyclopropane carboxylate was used in place of methyl=(1R)-trans-3-[(1EZ)-2-cyano-2-(ethylthio)ethenyl]-2,2-dimethylcyclopropane carboxylate, (1R)-trans-3-[(1EZ)-2-cyano-2-(butylthio)ethenyl]-2,2-dimethylcyclopropanecarboxylic acid represented by the following formula:

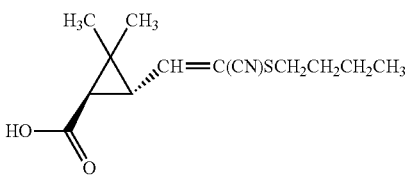

was obtained.

Pale yellow solid: $^1$H-NMR(CDCl$_3$, TMS) δ (ppm): 0.99 to 1.04 (m, 3H), 1.25+1.26 (s+s, 3H), 1.36+1.37 (s+s, 3H), 1.40 to 1.70 (m, 4H), 1.79 to 1.83 (m, 1H), 2.53 to 2.58 (m, 1H), 2.81 to 2.92 (m, 2H), 6.22 to 6.28 (m, 1H)

Reference Production Example 10

The reaction was conducted in the same manner as Reference Production Example 3, except that isopropyl mercaptan was used in place of ethyl mercaptan, methyl=(1R)-trans-3-[(1EZ)-2-cyano-2-(isopropylthio)ethenyl]-2,2-dimethylcyclopropane carboxylate represented by the following formula:

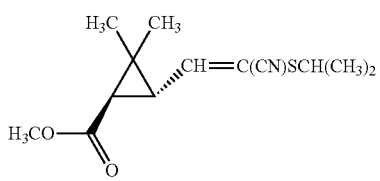

was obtained.

Colorless liquid: $^1$H-NMR(CDCl$_3$, TMS) δ (ppm): 1.23 to 1.39 (m, 12H), 1.81 to 1.85 (m, 1H), 2.51 to 2.62 (m, 1H), 3.31 to 3.45 (m, 1H), 3.71+3.72 (s+s, 3H), 6.27 to 6.36 (m, 1H)

Reference Production Example 11

The reaction was conducted in the same manner as Reference Production Example 4, except that methyl=(1R)-trans-3-[(1EZ)-2-cyano-2-(isopropylthio)ethenyl]-2,2-dimethylcyclopropane carboxylate was used in place of methyl=(1R)-trans-3-[(1EZ)-2-cyano-2-(ethylthio)ethenyl]-2,2-dimethylcyclopropane carboxylate, (1R)-trans-3-[(1EZ)-2-cyano-2-(isopropylthio)ethenyl]-2,2-dimethylcyclopropanecarboxylic acid represented by the following formula:

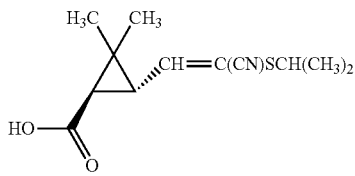

was obtained.

Reference Production Example 12

(1R)-4-hydroxy-6,6-dimethyl-3-oxabicyclo[3.1.0]hexan-2-one (1.585 g, 11.2 mmol), methylthioacetonitrile (1.30 g, 14.9 mmol) and potassium carbonate (1.85 g, 13.4 mmol) were added to N,N-dimethylformamide (15 mL), followed by stirring it at 20° C. for 48 hours. The reaction mixture was added to ice water (50 mL), and the solution was extracted with ethyl acetate (50 mL). To the obtained aqueous layer, 5% hydrochloric acid was added until the pH became 2, and then the aqueous layer was extracted twice with ethyl acetate (60 ml each). The obtained ethyl acetate layers were combined, washed once with saturated brine (50 mL) and then dried over magnesium sulfate. After concentration of the organic layer under reduced pressure, 2.30 g of 2-((1S,5R)-6,6-dimethyl-4-oxo-3-oxabicyclo[3.1.0]hexan-2-yl)-2-(methylthio)acetonitrile represented by the following formula:

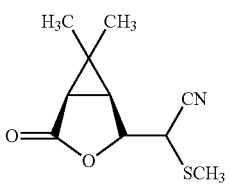

was obtained.

Pale yellow liquid: $^1$H-NMR(CDCl$_3$, TMS) δ (ppm): 1.22 to 1.31 (m, 6H), 1.44 (m, 1H), 1.77 (m, 1H), 2.35 (s, 1.5H), 2.38 (s, 1.5H), 3.60 (d, 0.5H), 3.64 (d, 0.5H), 4.23 (m, 0.5H), 4.33 (m, 0.5H)

Formulation Examples are shown below. Parts are by mass.

Formulation Example 1

Twenty (20) parts of each of the compounds (1) to (5) of the present invention is dissolved in 65 parts of xylene and 15 parts of SOLPOL 3005X (a registered trademark of TOHO Chemical Industry Co., Ltd.) is added thereto and thoroughly mixed with stirring to obtain emulsifiable concentrates.

Formulation Example 2

Five (5) parts of SORPOL 3005X is added to 40 parts of each of the compounds (1) to (5) of the present invention and the mixture is thoroughly mixed, and 32 parts of CARPLEX #80 (synthetic hydrated silicon oxide, a registered trademark of SHIONOGI & CO., LTD.) and 23 parts of 300-mesh diatomaceous earth are added thereto, followed by mixing with stirring by a mixer to obtain wettable powders.

Formulation Example 3

A mixture of 1.5 parts of each of the compounds (1) to (5) of the present invention, 1 part of TOKUSIL GUN (synthetic hydrated silicon oxide, manufactured by Tokuyama Corporation), 2 parts of REAX 85A (sodium lignin sulfonate, manufactured by West Vaco Chemicals), 30 parts of BENTONITE FUJI (bentonite, manufactured by Houjun) and 65.5 parts of SHOUKOUZAN A clay (kaoline clay, manufactured by Shoukouzan Kougyousho) is thoroughly pulverized and mixed, and water is added thereto. The mixture is thoroughly kneaded, granulated by an extruding granulator, and then dried to obtain 1.5% granules.

Formulation Example 4

To a mixture of 10 parts of each of the compounds (1) to (5) of the present invention, 10 parts of phenylxylylethane and 0.5 part of SUMIDUR L-75 (tolylene diisocyanate, manufactured by Sumitomo Bayer Urethane Co., Ltd.) is added 20 parts of 10% aqueous solution of gum arabic, and the mixture is stirred with a homomixer to obtain an emulsion having an average particle diameter of 20 μm. To the emulsion, 2 parts of ethylene glycol is added and the mixture is further stirred in a warm bath at a temperature of 60° C. for 24 hours to obtain microcapsule slurry. On the other hand, 0.2 part of xanthan gum and 1.0 part of VEEGUM R (aluminum magnesium silicate, manufactured by Sanyo Chemical Industries, Ltd.) are dispersed in 56.3 parts of ion-exchanged water to obtain a thickener solution. Then, 42.5 parts of the above-mentioned microcapsule slurry and 57.5 parts of the above-mentioned thickener solution are mixed to obtain microcapsules.

Formulation Example 5

A mixture of 10 parts of each of the compounds (1) to (5) of the present invention and 10 parts of phenylxylylethane is added to 20 parts of a 10% aqueous solution of polyethylene glycol, and the mixture is stirred by a homomixer to obtain an emulsion having an average particle diameter of 3 μm. On the other hand, 0.2 part of xanthan gum and 1.0 part of VEEGUM R (aluminum magnesium silicate, manufactured by Sanyo Chemical Industries, Ltd.) are dispersed in 58.8 parts of ion-exchanged water to obtain a thickener solution. Then, 40 parts of the above-mentioned emulsion solution and 60 parts of the above-mentioned thickener solution are mixed to obtain flowable formulations.

Formulation Example 6

To 5 parts of each of the compounds (1) to (5) of the present invention, 3 parts of CARPLEX #80 (synthetic hydrated silicon oxide, a registered trademark of SHIONOGI & CO., LTD.), 0.3 part of PAP (a mixture of monoisopropyl phosphate and diisopropyl phosphate) and 91.7 parts of talc (300 mesh) are added and the mixture is stirred by a mixer to obtain dusts.

Formulation Example 7

Zero point one (0.1) part of each of the compounds (1) to (5) of the present invention is dissolved in 10 parts of dichloromethane and the solution is mixed with 89.9 parts of deodorized kerosine to obtain oil solutions.

Formulation Example 8

Zero point one (0.1) part of each of the compounds (1) to (5) of the present invention and 39.9 parts of deodorized kerosene are mixed and dissolved, and the solution is filled into an aerosol container and a valve portion is installed. Then, 60 parts of power propellant (liquefied petroleum gas) is filled therein under pressure through the valve portion to obtain oil-based aerosol formulations.

Formulation Example 9

Zero point six (0.6) part of each of the compounds (1) to (5) of the present invention, 5 parts of xylene, 3.4 parts of deodorized kerosene and 1 part of Reodol MO-60 (emulsifier, a registered trademark of Kao Corporation) are mixed and dissolved, and the solution and 50 parts of water are filled into an aerosol container, and then 40 parts of power propellant (liquefied petroleum gas) is filled therein under pressure through a valve portion to obtain aqueous aerosol formulations.

Formulation Example 10

Zero point three (0.3) g of each of the compounds (1) to (5) of the present invention is dissolved in 20 ml of acetone and the solution is uniformly mixed with stirring with 99.7 g of a base material for a coil (obtained by mixing Tabu powder, Pyrethrum marc and wooden powder at a ratio of 4:3:3). Then, 100 ml of water is added thereto, and the mixture is thoroughly kneaded, dried and molded to obtain insecticidal coils.

Formulation Example 11

A mixture of 0.8 g of each of the compounds (1) to (5) of the present invention and 0.4 g of piperonyl butoxide is dissolved in acetone and the total volume is adjusted to 10 ml. Then, 0.5 ml of this solution is uniformly impregnated into a base material for an insecticidal mat for electric heating (a plate obtained by hardening fibrils of a mixture of cotton linters and pulp) having a size of 2.5 cm×1.5 cm and a thickness of 0.3 cm to obtain insecticidal mats for electric heating.

Formulation Example 12

A solution obtained by dissolving 3 parts of each of the compound (1) to (5) of the present invention in 97 parts of deodorized kerosine is poured into a vessel made of vinyl chloride. A liquid absorptive core whose upper part can be heated by a heater (an inorganic pulverized powder is hardened with a binder and sintered) is inserted thereinto to obtain parts to be used for a liquid absorptive core type thermal transpiring apparatus.

Formulation Example 13

One hundred (100) mg of each of the compound (1) to (5) of the present invention is dissolved in an appropriate amount of acetone and the solution is impregnated into a porous ceramic plate having a size of 4.0 cm×4.0 cm and a thickness of 1.2 cm to obtain thermal fumigants.

Formulation Example 14

One hundred (100) pg of each of the compound (1) to (5) of the present invention is dissolved in an appropriate amount of acetone and the solution is uniformly applied to filter paper having a size of 2 cm×2 cm and a thickness of 0.3 mm, and air-dried to remove acetone, and thus volatile agents for using at room temperature are obtained.

Formulation Example 15

Ten (10) parts of each of the compound of the present inventions (1) to (5), 35 parts of white carbon containing 50 parts of a polyoxyethylene alkyl ether sulfate ammonium salt, and 55 parts of water are mixed and then finely ground by a wet grinding method to obtain 10% formulations.

The following Test Examples illustrate that the compounds of the present invention are effective as an active ingredient of a pest control agent.

Test Example 1

Zero point one (0.1) part of the compound of the present inventions (1) was dissolved in 10 parts of isopropyl alcohol and the solution was mixed with 89.9 parts of deodorized kerosene to prepare a 0.1% (w/v) oil solution.

Six adult American cockroaches (*Periplaneta Americana*, 3 males and 3 females) were released in a test container (diameter 12.5 cm, 10 cm high, the bottom face is made of 16 mesh metallic wire), the inner face on which butter was applied, and the container was set at the bottom of a test chamber (bottom face: 46 cm×46 cm, height: 70 cm). One point five (1.5) ml of the oil solution of the compound of the present invention (1) was sprayed using a spray gun at a pressure of 0.4 kg/cm² from 60 cm higher than the upper face of the container. Thirty seconds after the spraying, the container was pulled out from the chamber. Ten minutes after spraying, the number of knocked-down cockroaches was counted and a knock-down ratio was determined (repeated twice). The knocked-down ratio was calculated by the following equation.

Knocked-down ratio (%)=(Number of knocked-down cockroaches/Number of test cockroaches)×100

The results (Ten minutes after spraying) are shown in Table 1.

TABLE 1

| Test compound | Knock-down ratio (%) 10 minutes after spraying |
|---|---|
| compound of the present invention (1) | 100 |

Test Example 2

Zero point one (0.1) part of the compound of the present inventions (1), (2),(3) and (5) was dissolved in 10 parts of isopropyl alcohol and the solution was mixed with 89.9 parts of deodorized kerosene to prepare a 0.1% (w/v) oil solution.

Ten adult German cockroaches (*Blattella germanica*, 5 males and 5 females) were released in a test container (diameter 8.75 cm, 7.5 cm high, the bottom face is made of 16 mesh metallic wire), the inner face on which butter was applied, and the container was set at the bottom of a test chamber (bottom face: 46 cm×46 cm, height: 70 cm).

Each 1.5 ml of the oil solution of the compound of the present invention (1), (2), (3) and (5) was sprayed using a spray gun at a pressure of 0.4 kg/cm² from 60 cm higher than the upper face of the container. Thirty seconds after the spraying, the container was pulled out from the chamber. Two minutes after spraying, the number of knocked-down cockroaches was counted and a knock-down ratio was determined (repeated once). A knocked-down ratio was calculated by the following equation.

Knocked-down ratio (%)=(Number of knocked-down cockroaches/Number of test cockroaches)×100

The results (2 minutes after spraying) are shown in Table 2.

TABLE 2

| Test compound | Knock-down ratio (%) 2 minutes after spraying |
|---|---|
| compound of the present invention (1) | 100 |
| compound of the present invention (2) | 100 |
| compound of the present invention (3) | 100 |
| compound of the present invention (5) | 100 |

Test Example 3

Zero point zero zero six two five(0.00625) part of the compound of the present invention (1) was dissolved in 10 parts of isopropyl alcohol, and the solution was mixed with 89.99375 parts of deodorized kerosene to prepare a 0.00625% (w/v) oil solution.

Ten adult female common mosquitoes (*Culex pipens pallens*) were released in a cubic glass chamber having each side of 70 cm. The oil solution of the compound of the present invention (1) was sprayed into the chamber through a small window on the side of the chamber using a spraying gun at a pressure of 0.9 kg/cm². Ten minutes after spraying, the number of knocked-down mosquitoes was counted and a knockdown ratio was determined. A knocked-down ratio was calculated by the following equation.

Knocked-down ratio (%)=(Number of knocked-down mosquitoes/Number of test mosquitoes)×100

TABLE 3

| Test compound | Knock-down ratio (%) 10 minutes after spraying |
|---|---|
| compound of the present invention (1) | 94 |

Test Example 4

Zero point zero zero six two five(0.00625) part of the compound of the present invention (1), (3) and (4) was dissolved in 10 parts of isopropyl alcohol, and the solution was mixed with 89.99375 parts of deodorized kerosene to prepare a 0.00625% (w/v) oil solution.

Ten adult houseflies (*Musca domestica*) were released in a cubic glass chamber having each side of 70 cm, and 0.7 ml of the oil solution of the compound of the present invention (1), (3) and (4) was sprayed into the chamber through a small window on the side of the chamber using a spraying gun at a pressure of 0.9 kg/cm². Seven minutes after spraying, the number of knocked-down flies was counted and a knockdown ratio was determined. A knocked-down ratio was calculated by the following equation.

Knocked-down ratio (%)=(Number of knocked-down flies/Number of test flies)×100

TABLE 4

| Test compound | Knock-down ratio (%) 7 minutes after spraying |
|---|---|
| compound of the present invention (1) | 100 |
| compound of the present invention (3) | 95 |
| compound of the present invention (4) | 95 |

Test Example 5

One (1) part of the compound of the present inventions (1) is dissolved in 10 parts of isopropyl alcohol and the solution is mixed with 89 parts of deodorized kerosene to prepare a 1% (w/v) oil solution.

Ten adult female common mosquitoes (*Culex pipens pallens*) are released in a test container (bottom diameter 10.5 cm, 7 cm high, 650 ml) and a top of the cup is covered with a net. The cup is set at the bottom of a test chamber (bottom face: 46 cm×46 cm, height: 70 cm). Zero point five (0.5) ml of the oil solution of the compound of the present invention (1) is sprayed using a spray gun at a pressure of 0.4 kg/cm² from 30 cm higher than the upper face of the cup. Immediately after spraying, the cup is pulled out from the test chamber. Two minutes after spraying, the number of knocked-down mosquitoes is counted and a knock-down ratio is determined.

Test Example 6

One (1) part of the compound of the present inventions (1) is dissolved in 10 parts of isopropyl alcohol and the solution is mixed with 89 parts of deodorized kerosene to prepare a 1% (w/v) oil solution.

Ten adult houseflies (*Musca domestica*) are released in a test container (bottom diameter 10.5 cm, 7 cm high, 650 ml) and a top of the cup was covered with a net. The cup is set at the bottom of a test chamber (bottom face: 46 cm×46 cm, height: 70 cm). Zero point five (0.5) ml of the oil solution of the compound of the present invention (1) is sprayed using a spray gun at a pressure of 0.4 kg/cm² from 30 cm higher than the upper face of the cup. Immediately after spraying, the cup is pulled out from the test chamber. Two minutes after spraying, the number of knocked-down houseflies is counted and a knock-down ratio is determined.

Test Example 7

One (1) part of the compound of the present inventions (1) is dissolved in 10 parts of isopropyl alcohol and the solution is mixed with 89 parts of deodorized kerosene to prepare a 1% (w/v) oil solution.

Six adult American cockroaches (*Periplaneta fuliginosa*, 3 males and 3 females) are released in a test container (diameter 12.5 cm, 10 cm high, the bottom face is made of 16 mesh metallic wire), the inner face on which butter is applied, and the container is set at the bottom of a test chamber (bottom face: 46 cm×46 cm, height: 70 cm). One point five (1.5) ml of the oil solution of the compound of the present invention (1) is sprayed using a spray gun at a pressure of 0.4 kg/cm² from 60 cm higher than the upper face of the container. Thirty seconds after the spraying, the container is pulled out from the chamber. One minutes after spraying, the number of knocked-down cockroaches is counted and a knock-down ratio is determined.

INDUSTRIAL APPLICABILITY

The compound of the present invention has an excellent pest control effect and is therefore useful as an active ingredient of a pest control agent.

The invention claimed is:
1. An ester compound represented by formula (I):

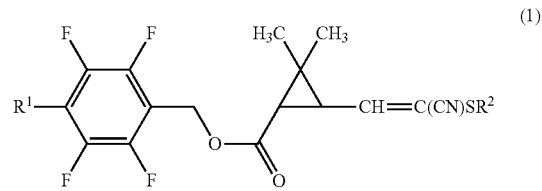

wherein $R^1$ represents hydrogen, fluorine, C1-C4 alkyl, C1-C4 alkoxy, C1-C4 alkoxymethyl, or C1-C4 alkylthiomethyl; and $R^2$ represents C1-C4 alkyl.

2. The ester compound according to claim 1, wherein a relative configuration of the substituent at the 1-position of the cyclopropane ring and the substituent at the 3-position of the cyclopropane ring is a trans configuration in formula (1).

3. The ester compound according to claim 1, wherein an absolute configuration of the 1-position of the cyclopropane ring is an R configuration in formula (1).

4. The ester compound according to claim 1, wherein an absolute configuration of the 1-position of the cyclopropane ring is an R configuration, and a relative configuration of the substituent at the 1-position of the cyclopropane ring and the substituent at the 3-position of the cyclopropane ring is a trans configuration in formula (1).

5. The ester compound according to claim 1, wherein a double bond of the substituent at the 3-position of the cyclopropane ring is in the E configuration or a mixture of E configuration and Z configuration, and the proportion of the E configuration is 50% or more in formula (1).

6. The ester compound according to claim 1, a double bond of the substituent at the 3-position of the cyclopropane ring is in the E configuration in formula (1).

7. The ester compound according to claim 1, wherein $R^2$ is methyl in formula (1).

8. The ester compound according to claim 1, wherein $R^2$ is ethyl in formula (1).

9. The ester compound according to claim 5, wherein $R^2$ is methyl in formula (1).

10. The ester compound according to claim 5, wherein $R^2$ is ethyl in formula (1).

11. The ester compound according to claim 6, wherein $R^2$ is methyl in formula (1).

12. The ester compound according to claim 6, wherein $R^2$ is ethyl in formula (1).

13. The ester compound according to claim 1, wherein $R^1$ is methoxymethyl in formula (1).

14. The ester compound according to claim 1, wherein $R^2$ is methyl in formula (1).

15. A pest control agent comprising the ester compound according to claim 1 and an inert carrier.

16. A method of controlling pests, which comprises a step of applying an effective amount of the ester compound according to claim 1 to pests or a place where pests habitat.

17. A method of controlling pests, which comprises the step of applying an effective amount of the ester compound according to claim 1 to cockroaches or a place where cockroaches inhabits.

18. The method of controlling pests according to claim 17, wherein the cockroach is American cockroach.

19. The method of controlling pests according to claim 17, wherein the cockroach is German cockroach.

20. A method of controlling pests, which comprises a step of spraying an effective amount of the ester compound according to claim 1 to cockroaches or a place where cockroaches inhabit.

21. The method of controlling pests according to claim 20, wherein the cockroach is American cockroach.

22. The method of controlling pests according to claim 20, wherein the cockroach is German cockroach.

* * * * *